United States Patent
Flom

(10) Patent No.: US 8,672,947 B2
(45) Date of Patent: Mar. 18, 2014

(54) METHOD AND APPARATUS FOR DISTRACTING A JOINT, INCLUDING THE PROVISION AND USE OF A NOVEL FLUID JOINT SPACER

(75) Inventor: James Flom, San Carlos, CA (US)

(73) Assignee: Pivot Medical, Inc., Sunnyvale, CA (US)

( * ) Notice: Subject to any disclaimer, the term of this patent is extended or adjusted under 35 U.S.C. 154(b) by 265 days.

(21) Appl. No.: 12/958,844

(22) Filed: Dec. 2, 2010

(65) Prior Publication Data

US 2011/0196378 A1 Aug. 11, 2011

Related U.S. Application Data

(60) Provisional application No. 61/283,303, filed on Dec. 2, 2009.

(51) Int. Cl.
*A61B 17/58* (2006.01)

(52) U.S. Cl.
USPC .............................................. 606/90; 606/192

(58) Field of Classification Search
USPC ........................................ 606/90, 191, 192
See application file for complete search history.

(56) References Cited

U.S. PATENT DOCUMENTS

| | | | | |
|---|---|---|---|---|
| 7,004,945 | B2 * | 2/2006 | Boyd et al. | 606/92 |
| 7,217,273 | B2 * | 5/2007 | Bonutti | 606/90 |
| 2006/0293685 | A1 * | 12/2006 | Stone et al. | 606/90 |
| 2010/0312179 | A1 * | 12/2010 | Nikolchev et al. | 604/96.01 |
| 2011/0190676 | A1 * | 8/2011 | Torrie et al. | 602/32 |

* cited by examiner

*Primary Examiner* — Nicholas Woodall
(74) *Attorney, Agent, or Firm* — Pandiscio & Pandiscio

(57) ABSTRACT

A fluid joint spacer comprising a body having means for receiving a pressurized fluid from an external source and applying that pressurized fluid against a joint element so as to create a flowing fluid bearing within the joint.

54 Claims, 27 Drawing Sheets

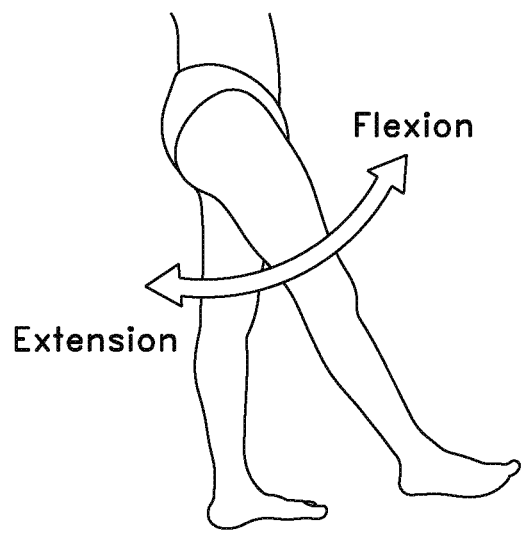
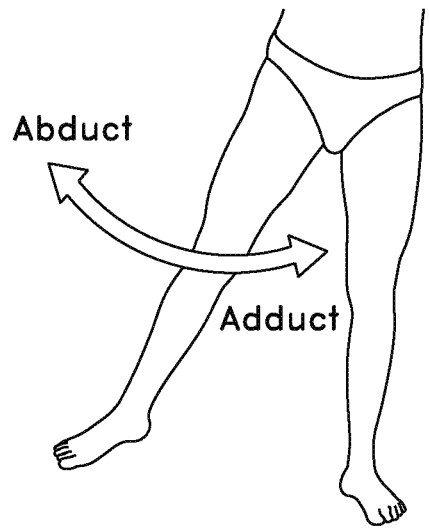
FIG. 1A   FIG. 1B
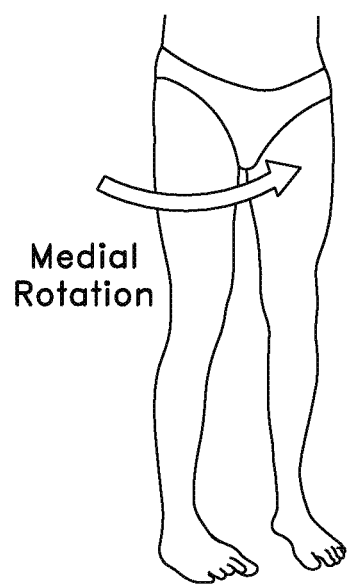
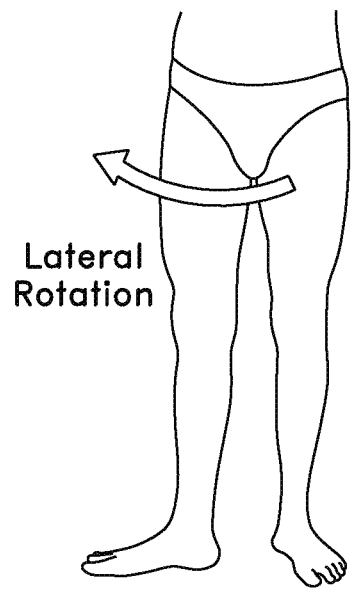
FIG. 1C   FIG. 1D

CAM-TYPE FEMOROACETABULAR IMPINGEMENT (FAI)

CAM INJURY TO THE LABRUM

PINCER-TYPE FEMOROACETABULAR IMPINGEMENT (FAI)

PINCER INJURY TO THE LABRUM

METHOD AND APPARATUS FOR DISTRACTING A JOINT, INCLUDING THE PROVISION AND USE OF A NOVEL FLUID JOINT SPACER

REFERENCE TO PENDING PRIOR PATENT APPLICATION

This patent application claims benefit of pending prior U.S. Provisional Patent Application Ser. No. 61/283,303, filed Dec. 2, 2009 by James Flom for FLUID JOINT SPACER, which patent application is hereby incorporated herein by reference.

FIELD OF THE INVENTION

This invention relates to surgical methods and apparatus in general, and more particularly to surgical methods and apparatus for treating a hip joint.

BACKGROUND OF THE INVENTION

The Hip Joint in General

The hip joint, is a ball-and-socket joint which movably connects the leg to the torso. The hip joint is capable of a wide range of different motions, e.g., flexion and extension, abduction and adduction, medial and lateral rotation, etc. See FIGS. 1A, 1B, 1C and 1D.

With the possible exception of the shoulder joint, the hip joint is perhaps the most mobile joint in the body. Significantly, and unlike the shoulder joint, the hip joint carries substantial weight loads during most of the day, in both static (e.g., standing and sitting) and dynamic (e.g., walking and running) conditions.

The hip joint, is susceptible to a number of different pathologies. These pathologies can have both congenital and injury-related origins. In some cases, the pathology can be substantial at the outset. In other cases, the pathology may be minor at the outset but, if left untreated, may worsen over time. More particularly, in many cases, an existing pathology may be exacerbated by the dynamic nature of the hip joint and the substantial weight loads imposed on the hip joint.

The pathology may, either initially or thereafter, significantly interfere with patient comfort and lifestyle. In some cases, the pathology can be so severe as to require partial or total hip replacement. A number of procedures have been developed for treating hip pathologies short of partial or total hip replacement, but these procedures are generally limited in scope due to the significant difficulties associated with treating the hip joint.

A better understanding of various hip joint pathologies, and also the current limitations associated with their treatment, can be gained from a more thorough understanding of the anatomy of the hip joint.

Anatomy of the Hip Joint

The hip joint is formed at the junction of the leg and the hip. More particularly, and looking now at FIG. 2, the head of the femur is received in the acetabular cup of the hip, with a plurality of ligaments and other soft tissue serving to hold the bones in articulating condition.

More particularly, and looking now at FIG. 3, the femur is generally characterized by an elongated body terminating, at its top end, in an angled neck which supports a hemispherical head (also sometimes referred to as "the ball"). As seen in FIGS. 3 and 4, a large projection known as the greater trochanter protrudes laterally and posteriorly from the elongated body adjacent to the neck of the femur. A second, somewhat smaller projection known as the lesser trochanter protrudes medially and posteriorly from the elongated body adjacent to the neck. An intertrochanteric crest (FIGS. 3 and 4) extends along the periphery of the femur, between the greater trochanter and the lesser trochanter.

Looking next at FIG. 5, the hip socket is made up of three constituent bones: the ilium, the ischium and the pubis. These three bones cooperate with one another (they typically ossify into a single "hip bone" structure by the age of 25 or so) in order to collectively form the acetabular cup. The acetabular cup receives the head of the femur.

Both the head of the femur and the acetabular cup are covered with a layer of articular cartilage which protects the underlying bone and facilitates motion. See FIG. 6.

Various ligaments and soft tissue serve to hold the ball of the femur in place within the acetabular cup. More particularly, and looking now at FIGS. 7 and 8, the ligamentum teres extends between the ball of the femur and the base of the acetabular cup. As seen in FIGS. 8 and 9, a labrum is disposed about the perimeter of the acetabular cup. The labrum serves to increase the depth of the acetabular cup and effectively establishes a suction seal between the ball of the femur and the rim of the acetabular cup, thereby helping to hold the head of the femur in the acetabular cup. In addition to the foregoing, and looking now at FIG. 10, a fibrous capsule extends between the neck of the femur and the rim of the acetabular cup, effectively sealing off the ball-and-socket members of the hip joint from the remainder of the body. The foregoing structures (i.e., the ligamentum teres, the labrum and the fibrous capsule) are encompassed and reinforced by a set of three main ligaments (i.e., the iliofemoral ligament, the ischiofemoral ligament and the pubofemoral ligament) which extend between the femur and the perimeter of the hip socket. See, for example, FIGS. 11 and 12, which show the iliofemoral ligament, with FIG. 11 being an anterior view and FIG. 12 being a posterior view.

Pathologies of the Hip Joint

As noted above, the hip joint is susceptible to a number of different pathologies. These pathologies can have both congenital and injury-related origins.

By way of example but not limitation, one important type of congenital pathology of the hip joint involves impingement between the neck of the femur and the rim of the acetabular cup. In some cases, and looking now at FIG. 13, this impingement can occur due to irregularities in the geometry of the femur. This type of impingement is sometimes referred to as cam-type femoroacetabular impingement (i.e., cam-type FAI). In other cases, and looking now at FIG. 14, the impingement can occur due to irregularities in the geometry of the acetabular cup. This latter type of impingement is sometimes referred to as pincer-type femoroacetabular impingement (i.e., pincer-type FAI). Impingement can result in a reduced range of motion, substantial pain and, in some cases, significant deterioration of the hip joint.

By way of further example but not limitation, another important type of congenital pathology of the hip joint involves defects in the articular surface of the ball and/or the articular surface of the acetabular cup. Defects of this type sometimes start out fairly small but often increase in size over time, generally due to the dynamic nature of the hip joint and also due to the weight-bearing nature of the hip joint. Articular defects can result in substantial pain, induce and/or exacerbate arthritic conditions and, in some cases, cause significant deterioration of the hip joint.

By way of further example but not limitation, one important type of injury-related pathology of the hip joint involves trauma to the labrum. More particularly, in many cases, an accident or sports-related injury can result in the labrum being torn away from the rim of the acetabular cup, typically with a tear running through the body of the labrum. See FIG. 15. These types of injuries can very painful for the patient and, if left untreated, can lead to substantial deterioration of the hip joint.

The General Trend Toward Treating Joint Pathologies Using Minimally-Invasive, and Earlier, Interventions The current trend in orthopedic surgery is to treat joint pathologies using minimally-invasive techniques. Such minimally-invasive, "keyhole" surgeries generally offer numerous advantages over traditional, "open" surgeries, including reduced trauma to tissue, less pain for the patient, faster recuperation times, etc.

By way of example but not limitation, it is common to re-attach ligaments in the shoulder joint using minimally-invasive, "keyhole" techniques which do not require laying open the capsule of the shoulder joint. By way of further example but not limitation, it is common to repair torn meniscal cartilage in the knee joint, and/or to replace ruptured ACL ligaments in the knee joint, using minimally-invasive techniques.

While such minimally-invasive approaches can require additional training on the part of the surgeon, such procedures generally offer substantial advantages for the patient and have now become the standard of care for many shoulder joint, and knee joint pathologies.

In addition to the foregoing, in view of the inherent advantages and widespread availability of minimally-invasive approaches for treating pathologies of the shoulder joint, and the knee joint, the current trend is to provide such treatment much earlier in the lifecycle of the pathology, so as to address patient pain as soon as possible and so as to minimize any exacerbation of the pathology itself. This is in marked contrast to traditional surgical practices, which have generally dictated postponing surgical procedures as long as possible so as to spare the patient from the substantial trauma generally associated with invasive surgery.

Treatment for Pathologies of the Hip Joint

Unfortunately, minimally-invasive treatments for pathologies of the hip joint have lagged far behind minimally-invasive treatments for pathologies of the shoulder joint and the knee joint. This is generally due to (i) the constrained geometry of the hip joint itself, and (ii) the nature and location of the pathologies which must typically be addressed in the hip joint.

More particularly, the hip joint is generally considered to be a "tight" joint, in the sense that there is relatively little room to maneuver within the confines of the joint itself. This is in marked contrast to the shoulder joint and the knee joint, which are generally considered to be relatively "spacious" joints (at least when compared to the hip joint). As a result, it is relatively difficult for surgeons to perform minimally-invasive procedures on the hip joint.

Furthermore, the pathways for entering the interior of the hip joint (i.e., the natural pathways which exist between adjacent bones and/or delicate neurovascular structures) are generally much more constraining for the hip joint than for the shoulder joint or the knee joint. This limited access further complicates effectively performing minimally-invasive procedures on the hip joint.

In addition to the foregoing, the nature and location of the pathologies of the hip joint also complicate performing minimally-invasive procedures on the hip joint. By way of example but not limitation, consider a typical detachment of the labrum in the hip joint. In this situation, instruments must generally be introduced into the joint space using an angle of approach which is offset from the angle at which the instrument addresses the tissue. This makes drilling into bone, for example, significantly more complicated than where the angle of approach is effectively aligned with the angle at which the instrument addresses the tissue, such as is frequently the case in the shoulder joint. Furthermore, the working space within the hip joint is typically extremely limited, further complicating repairs where the angle of approach is not aligned with the angle at which the instrument addresses the tissue.

As a result of the foregoing, minimally-invasive hip joint procedures are still relatively difficult to perform and relatively uncommon in practice. Consequently, patients are typically forced to manage their hip pain for as long as possible, until a resurfacing procedure or a partial or total hip replacement procedure can no longer be avoided. These procedures are generally then performed as a highly-invasive, open procedure, with all of the disadvantages associated with highly-invasive, open procedures.

As a result, there is, in general, a pressing need for improved methods and apparatus for treating pathologies of the hip joint.

Current Approaches for Hip Joint Distraction

During arthroscopic hip surgery, it is common to distract the hip joint so as to provide increased workspace within the joint. More particularly, during arthroscopic hip surgery, it is common to unseat the ball of the femur from the socket of the acetabular cup so as to provide (i) improved access to the interior of the joint, (ii) additional workspace within the interior of the joint, and (iii) increased visibility for the surgeon during the procedure. This hip joint distraction is normally accomplished in the same manner that the hip joint is distracted during a total hip replacement procedure, e.g., by gripping the lower end of the patient's leg near the ankle and then pulling the leg distally with substantial force so as to unseat the bail of the femur from the acetabular cup.

However, since the distracting force is applied to the lower end of the patient's leg, this approach necessitates that the distracting force be applied across substantially the entire length of the leg. As a result, the intervening tissue (i.e., the tissue located between where the distracting force is applied and the ball of the femur) must bear the distracting load for the entire time that the hip joint is distracted.

In practice, it has been found that the longer the distracting load is maintained on the leg, the greater the trauma imposed on the intervening tissue. Specifically, it has been found that temporary or even permanent neurological damage can occur if the leg is distracted for too long using conventional distraction techniques.

As a result, the standard of care in the field is for the surgeon to limit the duration of distraction during arthroscopic hip surgery to 90 minutes or less in order to minimize damage to the intervening tissue due to joint distraction. In some situations, this can mean that desirable therapeutic procedures may be curtailed, or even eliminated entirely, in order to keep the duration of the distraction to 90 minutes or less. And even where the duration of the distraction is kept to 90 minutes or less, significant complications can nonetheless occur for many patients.

In addition to the foregoing, in current hip distraction, it is common to use a perineal post to facilitate hip distraction.

More particularly, and looking now at FIG. 16, a perineal post is generally positioned between the legs of the patient so that the medial side of the femur which is to be distracted lies against the perineal post. After the patient's leg is pulled distally (i.e., in the direction of the pulling vector $V_P$), the leg is adducted so as to lever the leg against the perineal post, which moves the neck and ball of the femur in the direction of the lateral vector $V_L$; the combination of these two displacements is $V_D$ (i.e., the resultant vector of the vectors of $V_L$ and $V_P$) This ensures that the ball of the femur is unseated from the acetabular cup in the desired direction (i.e., in the direction of the resultant vector $V_D$).

Unfortunately, it has been found that the use of a perineal post can contribute to the damage done to the intervening tissue when the leg is distracted too long. This is because the perineal post can press against the pudendal nerve and/or the sciatic nerve (as well as other anatomy) when distraction occurs. Thus, if the distraction is held too long, neurological damage can occur. This is another reason that the standard of care in the field is for the surgeon to limit the duration of distraction during arthroscopic hip surgery to 90 minutes or less. Additionally, the perineal post can exert pressure on the blood vessels in the leg, and it has been shown that blood flow in these vessels (e.g., the femoral vein, etc.) can be reduced, or in some cases completely occluded, while the hip is in distraction, thus placing the patient in danger of forming deep vein thrombosis or developing other complications.

Additionally, current hip distraction limits the extent to which the leg can be manipulated under distraction during hip arthroscopy, since a substantial pulling force must be maintained on the distal end of the leg throughout the duration of the distraction. Due to this, and due to the fact that there are typically only 2-4 portals available for surgical access into the interior of the hip joint, visualization and access to hip joint pathology and anatomy is frequently hindered. This can limit the extent of surgical procedures available to the surgeon, and can prevent some procedures from being attempted altogether. Procedures such as mosaicplasty and autologous cartilage injection are examples of procedures which require access to extensive areas of the articular surfaces of the femoral head, but which are typically not performed arthroscopically because of the aforementioned access limitations due to leg distraction.

Thus, there is a need for a new and improved approach for distracting the hip joint which addresses the foregoing problems.

SUMMARY OF THE INVENTION

These and other objects of the present invention are addressed by the provision and use of a new method and apparatus for distracting a joint.

Among other things, the present invention provides a novel method for distracting a joint and for maintaining distraction of a joint, wherein the novel method minimizes damage to intervening tissue while maintaining distraction of the joint. In addition, the novel method allows visualization of areas in the joint that were not previously visible using a conventional distraction approach.

The present invention also provides novel apparatus for distracting a joint, and for maintaining distraction of a joint, wherein the novel apparatus comprises a novel fluid joint spacer for maintaining the distraction of a joint.

In one preferred form of the invention, there is provided a method for creating space in a joint, the method comprising:
 applying force to a body part so as to distract the joint and create an intrajoint space;
 establishing a flowing fluid bearing within the intrajoint space; and
 reducing the force applied to the body part so that the joint is supported on the flowing fluid bearing.

In another preferred form of the invention, there is provided a method for maintaining space in a distracted joint, the method comprising:
 inserting a fluid joint spacer into the interior of the distracted joint; and
 passing pressurized fluid through the fluid joint spacer so as to maintain the distraction of the joint.

In another preferred form of the invention, there is provided a method for creating space in a joint, the method comprising:
 inserting a fluid joint spacer into the interior of the joint; and
 passing pressurized fluid through the fluid joint spacer so as to create an intrajoint space.

In another preferred form of the invention, there is provided a fluid joint spacer comprising:
 a body having means for receiving a pressurized fluid from an external source and applying that pressurized fluid against a joint element so as to create a flowing fluid bearing within the joint.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 1A-1D are schematic views showing various aspects of hip motion;

DETAILED DESCRIPTION OF THE PREFERRED EMBODIMENTS

Novel Fluid Joint Spacer

In one form of the present invention, there is provided a novel fluid joint spacer which may be used to maintain the distraction of a joint, as will hereinafter be discussed in detail.

Figure 17:
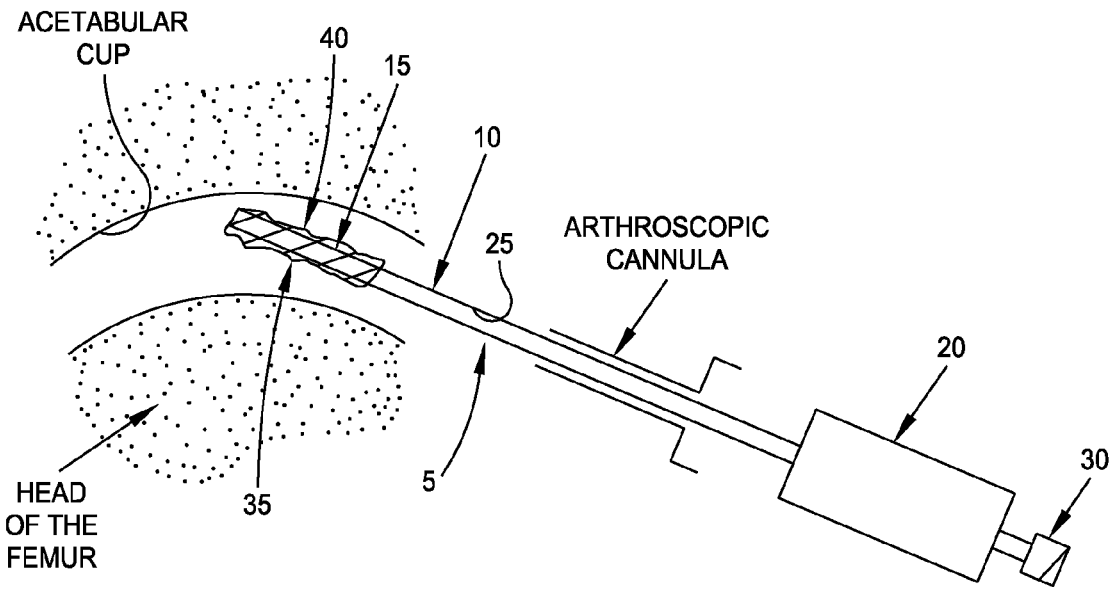
FIGS. 17-23 are schematic views showing the construction and preferred methods of use for a first embodiment of the fluid joint spacer of the present invention.
Figure 18:
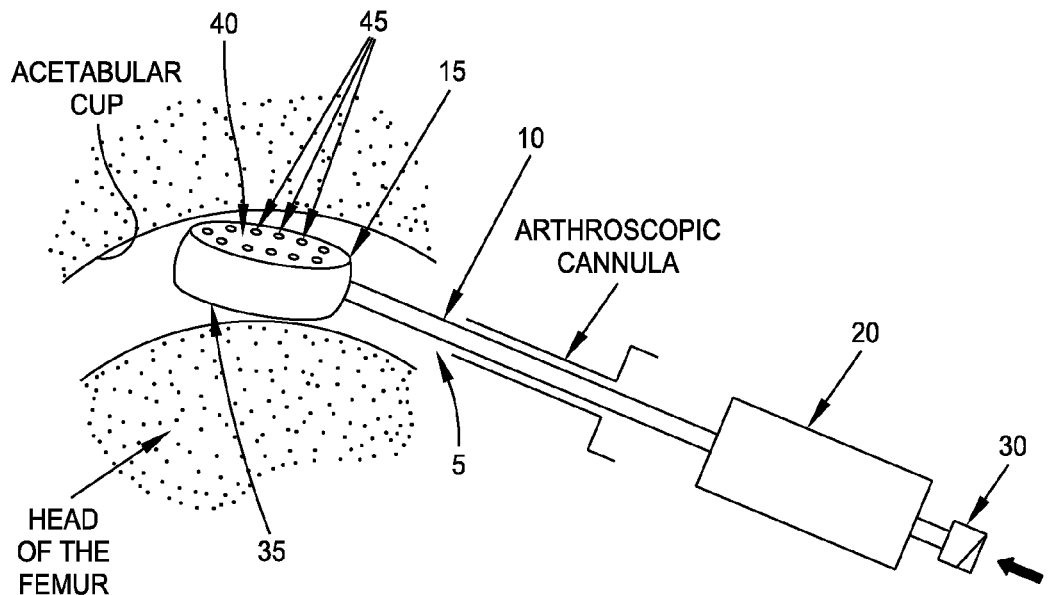
Figure 19:
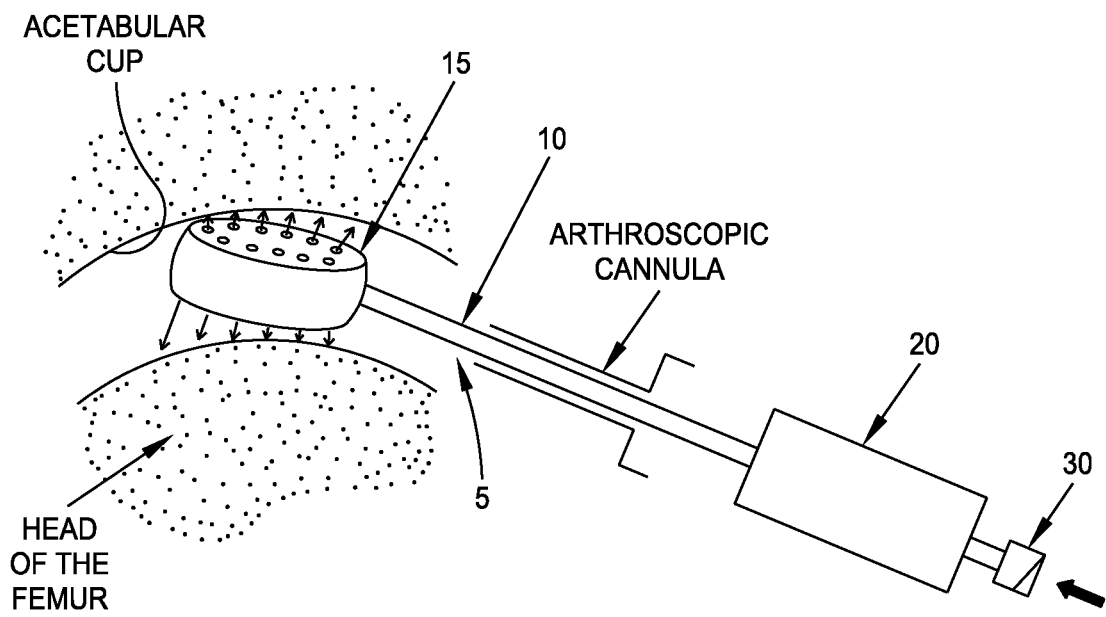

More particularly, in this form of the invention, and looking next at FIGS. 17-19, there is shown a novel fluid joint spacer 5 formed in accordance with the present invention. Novel fluid joint spacer 5 generally comprises an elongated shaft 10 having a body 15 disposed at its distal end and a handle 20 disposed at its proximal end. A lumen 25 connects the interior of body 15 with a fluid fitting 30 disposed on handle 20.

Elongated shaft 10 may be rigid or bendable and, if it is bendable, it may be steerable via means (not shown) provided on handle 20. In any case, elongated shaft 10 has sufficient structural integrity along its length so as to facilitate proper positioning of body 15 via handle 20 during use.

In this form of the invention, body 15 comprises a balloon structure having a first surface 35 for disposition adjacent the head of the femur, and a second surface 40 for disposition adjacent the acetabular cup. A plurality of openings 45 are formed in first surface 35 and/or second surface 40 so that fluid introduced into fluid fitting 30 will pass through lumen 25, inflate the balloon structure of body 15 and then pass out openings 45, whereby to apply fluid pressure against the head of the femur and/or the acetabular cup. In accordance with the present invention, this fluid is introduced into fluid fitting 30 with a sufficient pressure that the fluid flowing out of fluid joint spacer 5 via openings 45 is able to maintain the distraction of a joint into which fluid joint spacer 5 is deployed.

If desired, the balloon structure of body 15 can be engineered so that when the balloon structure has been inflated with fluid, first surface 35 and second surface 40 will assume substantially planar configurations. See FIGS. 17-19. Alternatively, the balloon structure of body 15 can be engineered so that when the balloon structure has been inflated with fluid, first surface 35 will assume a concave shape so as to complement the ball of the femur and/or second surface 40 will assume a convex shape so as to complement the shape of the acetabular cup. Furthermore, if desired, balloon 15 can include an atraumatic tip at its distal end so as to minimize tissue damage during insertion of the device into the joint space, movement of the device within the joint space, etc.

On account of the foregoing, handle 20 can be used to direct shaft 10 so that body 15 is advanced into the hip joint while the balloon structure of body 15 is in its deflated condition, and then fluid joint spacer 5 may have the balloon structure of the body 15 inflated by introducing fluid into fluid fitting 30, whereupon fluid will flow through lumen 25 and out openings 45, whereby to apply pressure against the head of the femur and/or the acetabular cup. By introducing this fluid into fluid fitting 30 with a sufficiently high pressure, the fluid flowing out of fluid joint spacer 5 via openings 45 is able to apply sufficient pressure to the adjacent structures so as to maintain the distraction of a joint, as will hereinafter be discussed in detail.

Thus it will be seen that, during use, the fluid joint spacer essentially provides a flowing fluid bearing to support a distraction of the joint. More particularly, where fluid joint, spacer 5 provides openings 45 on its first surface 35 but not on its second surface 40, the fluid joint spacer will seat its second surface 40 against, the acetabular cup and support the head of the femur on the pressurized fluid flow emerging from openings 45; where fluid joint spacer 5 provides openings 45 on its second surface 40 but not on its first surface 35, the fluid joint spacer will seat its first surface 35 on the head of the femur and support the acetablular cup on the pressurized fluid flow emerging from openings 45; and where fluid joint spacer 5 provides openings 45 on both its first surface 35 and its second surface 40, the fluid joint spacer will support the head of the femur and the acetabular cup on the pressurized fluid flow emerging from openings 45.

It will be appreciated that openings 45 may have a variety of configurations. In general, such configurations are chosen so as to apply maximum fluid pressure to the anatomy without causing trauma to the anatomy.

Novel Method for Distracting a Joint

In another form of the present invention, there is provided a novel method for distracting a joint, preferably the hip joint, and preferably using novel fluid joint spacer 5.

Figure 2:
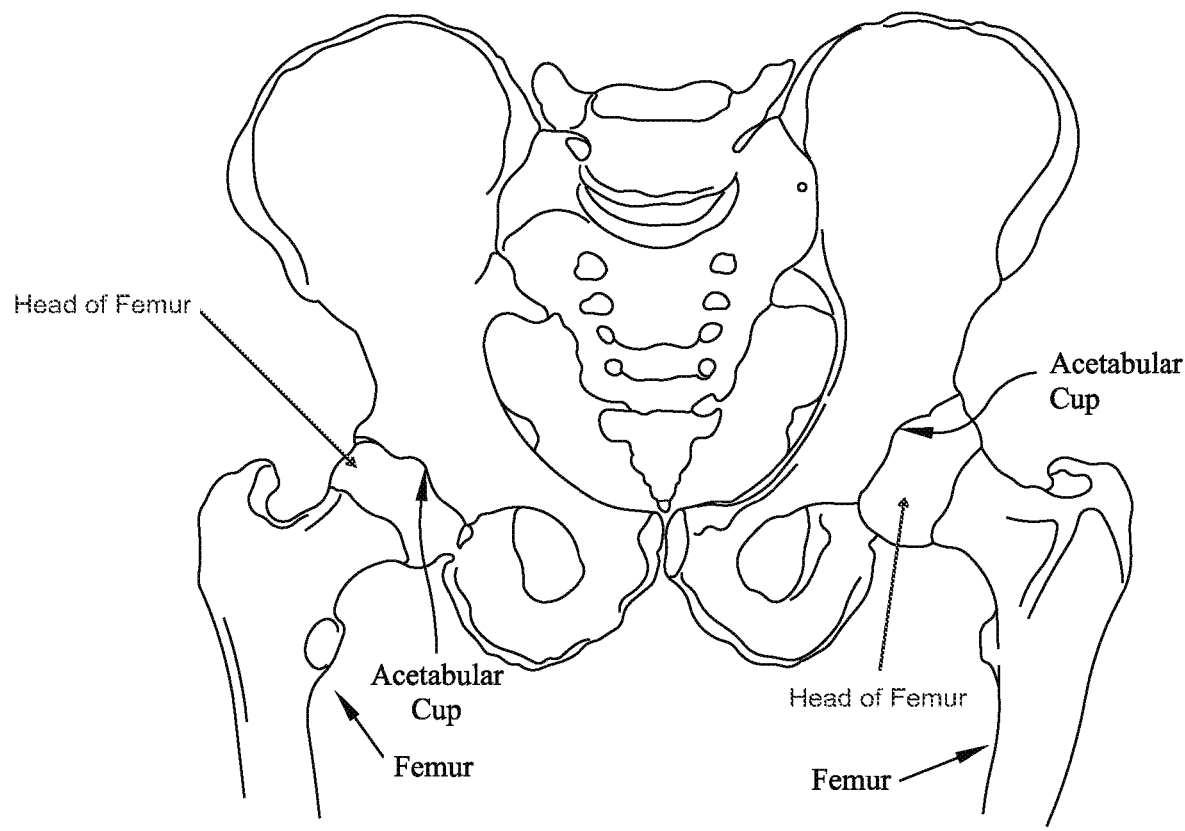
FIG. 2 is a schematic view showing the bone structure in the region of the hip joints.
Figure 3:
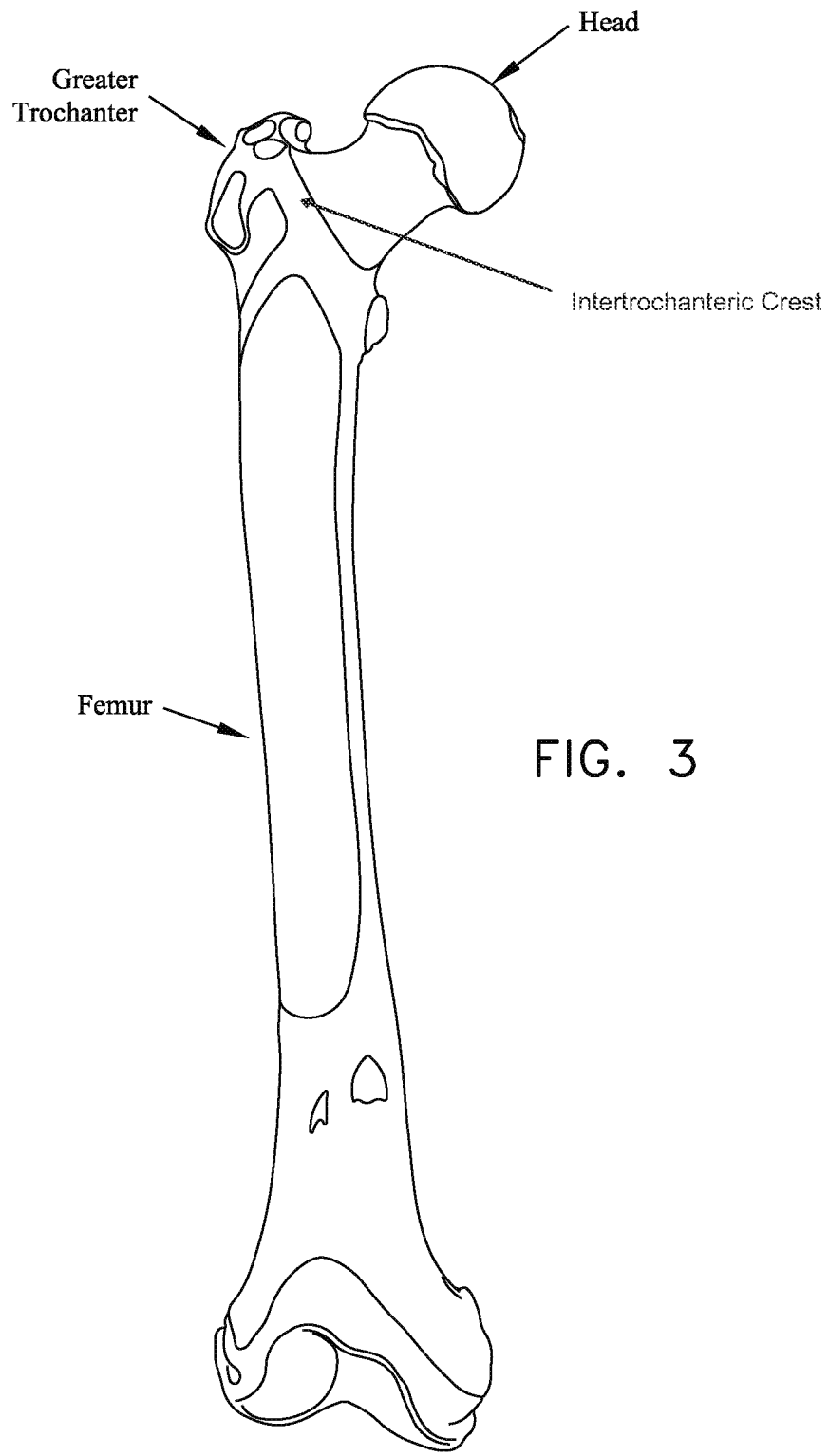
FIG. 3 is a schematic anterior view of the femur.
Figure 4:
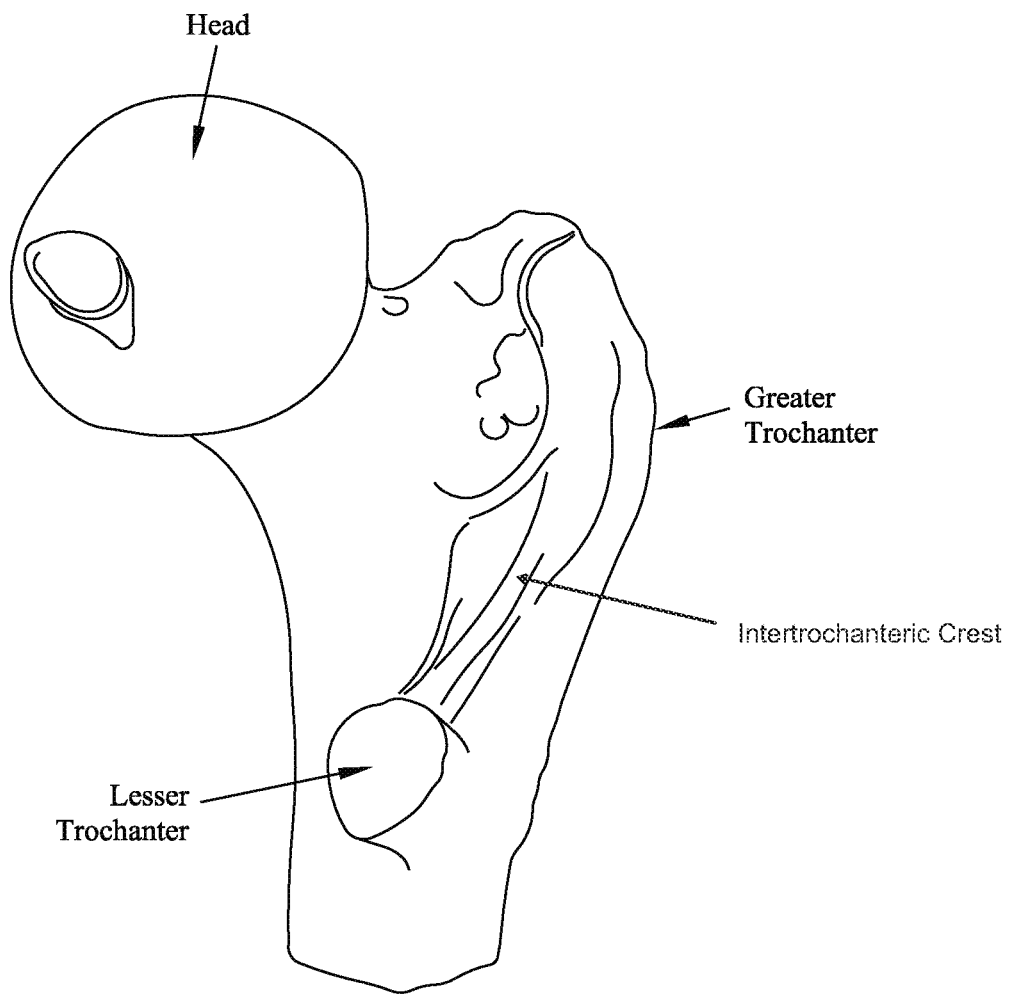
FIG. 4 is a schematic posterior view of the top end of the femur.
Figure 5:
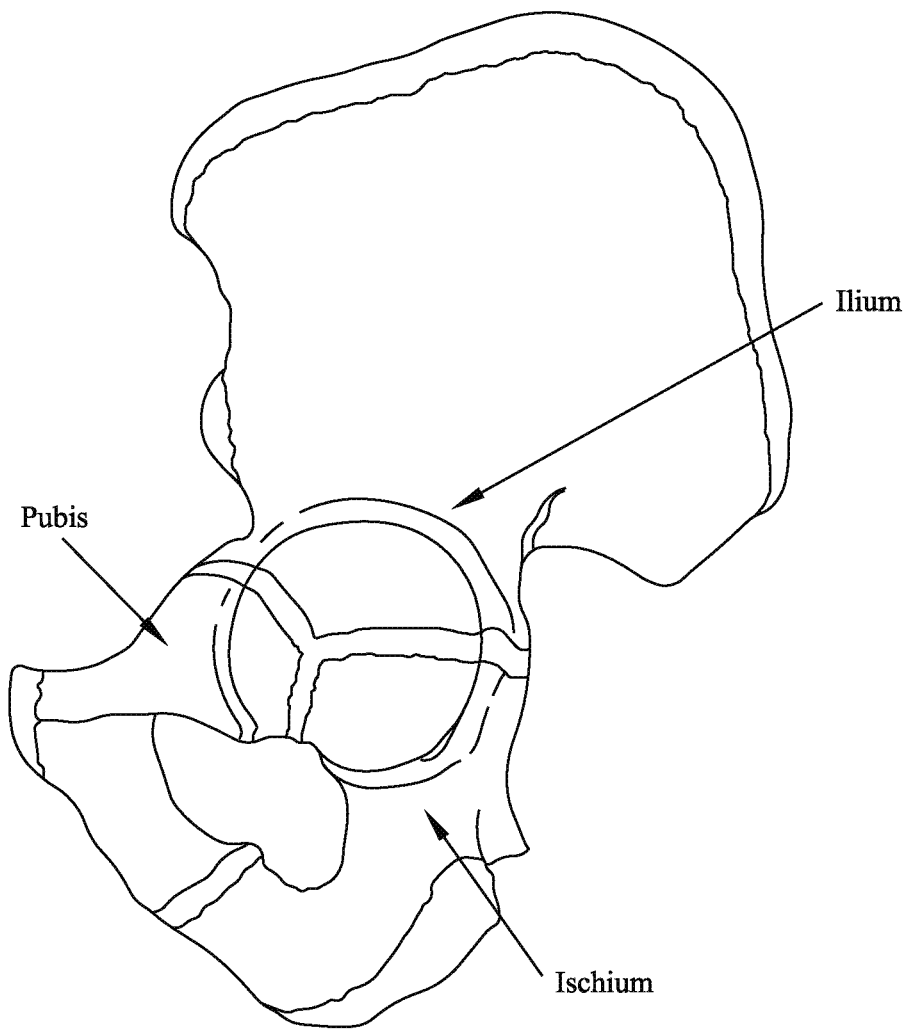
FIG. 5 is a schematic view of the pelvis.
Figure 6:
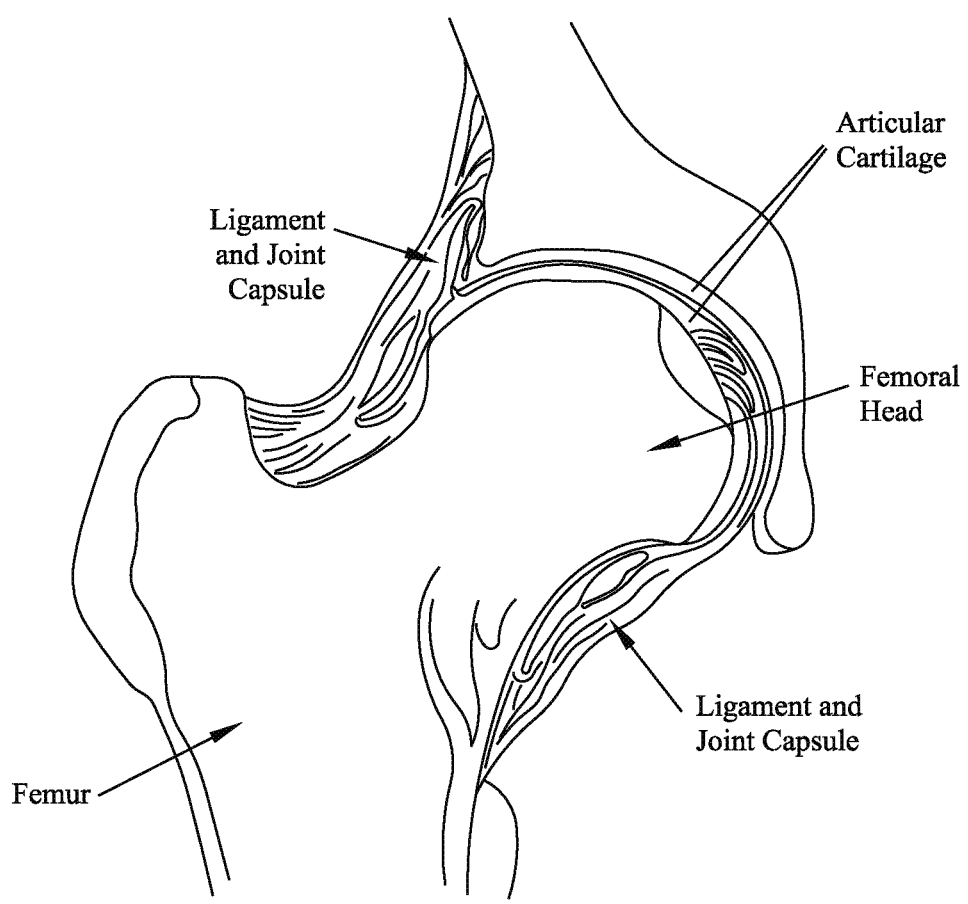
FIGS. 6-12 are schematic views showing the bone and soft tissue structure of the hip joint.
Figure 7:
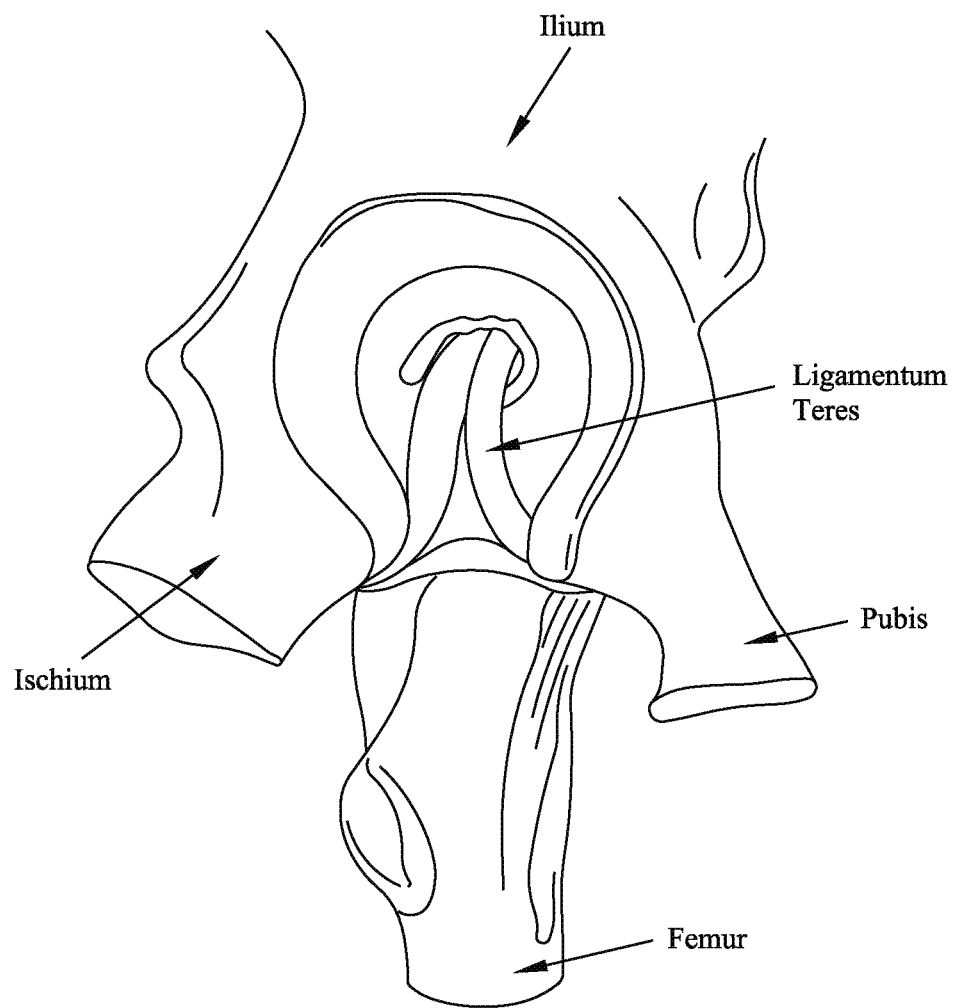
Figure 8:
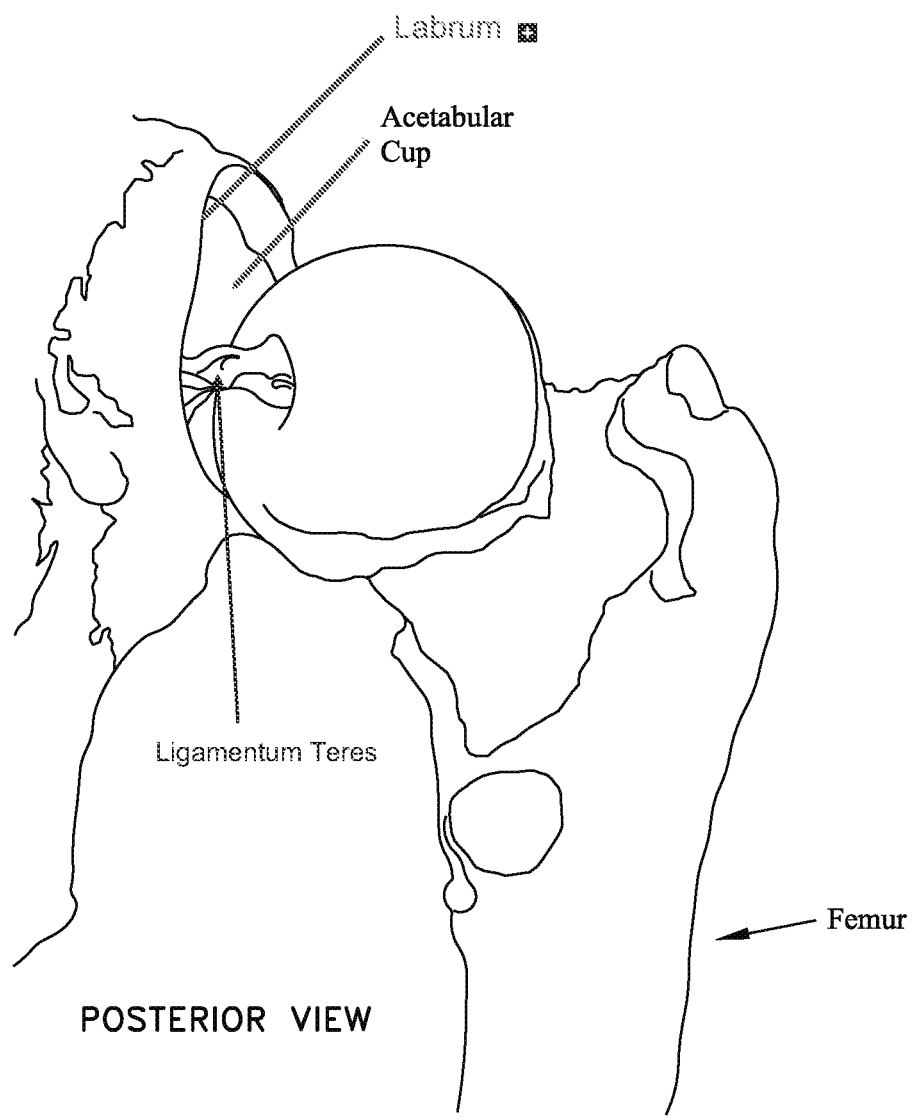
Figure 9:
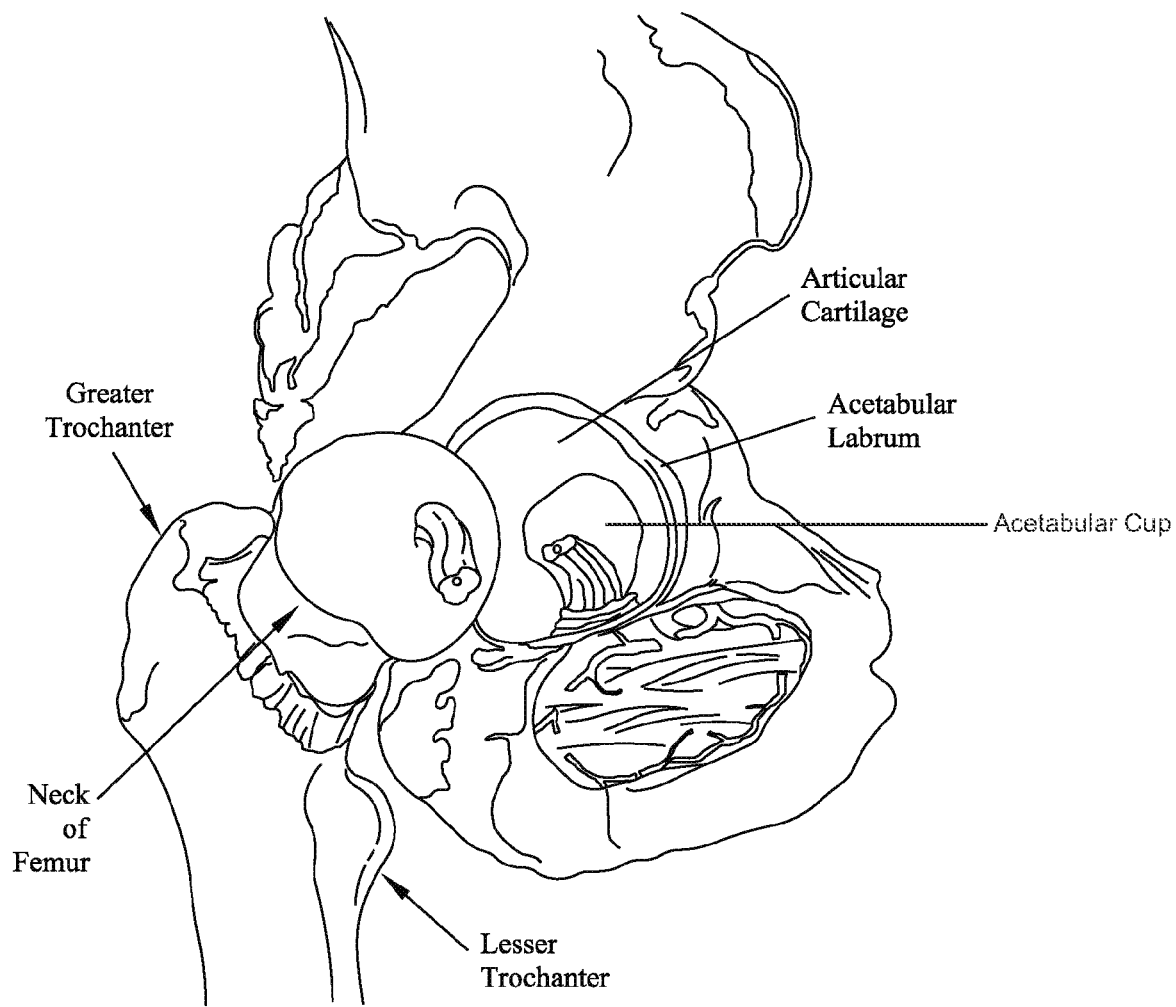
Figure 10:
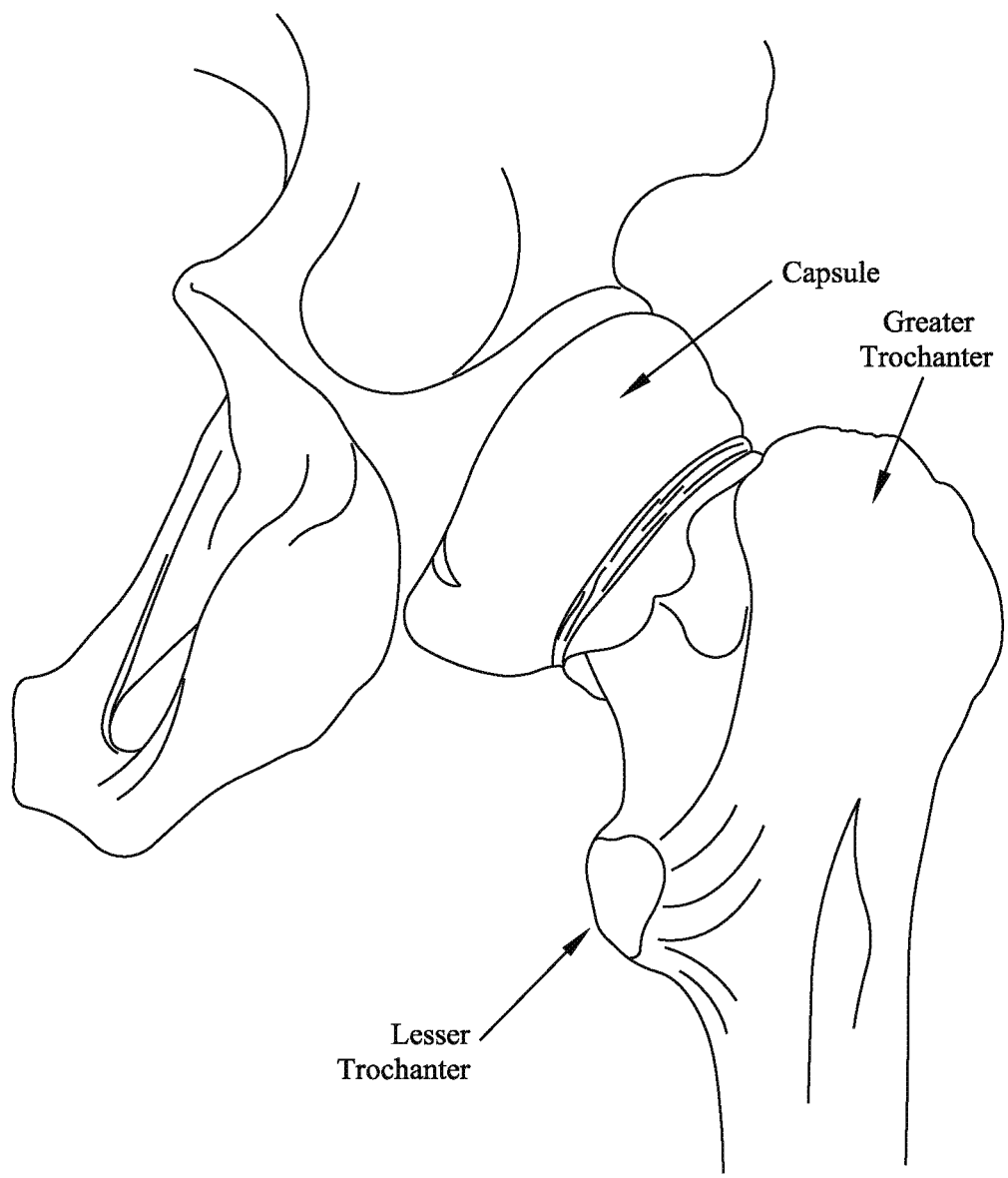
Figure 11:
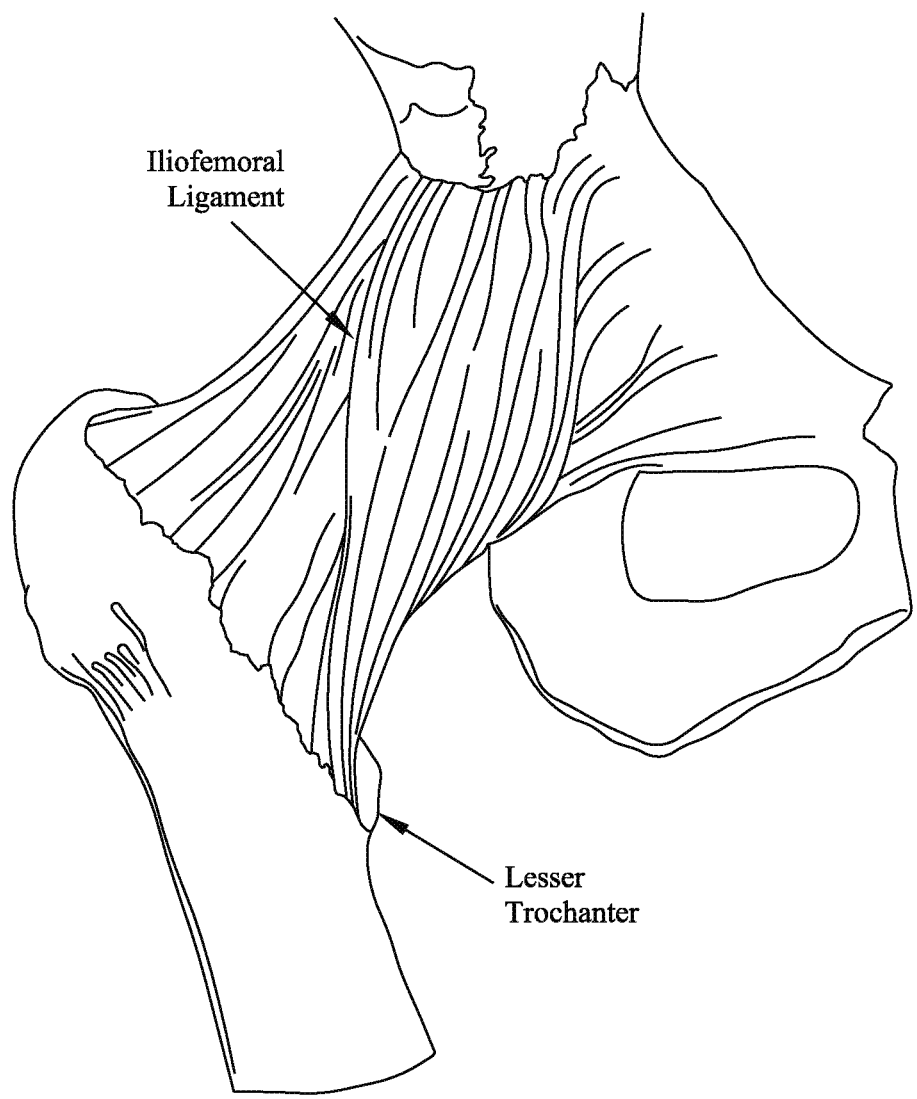
Figure 12:
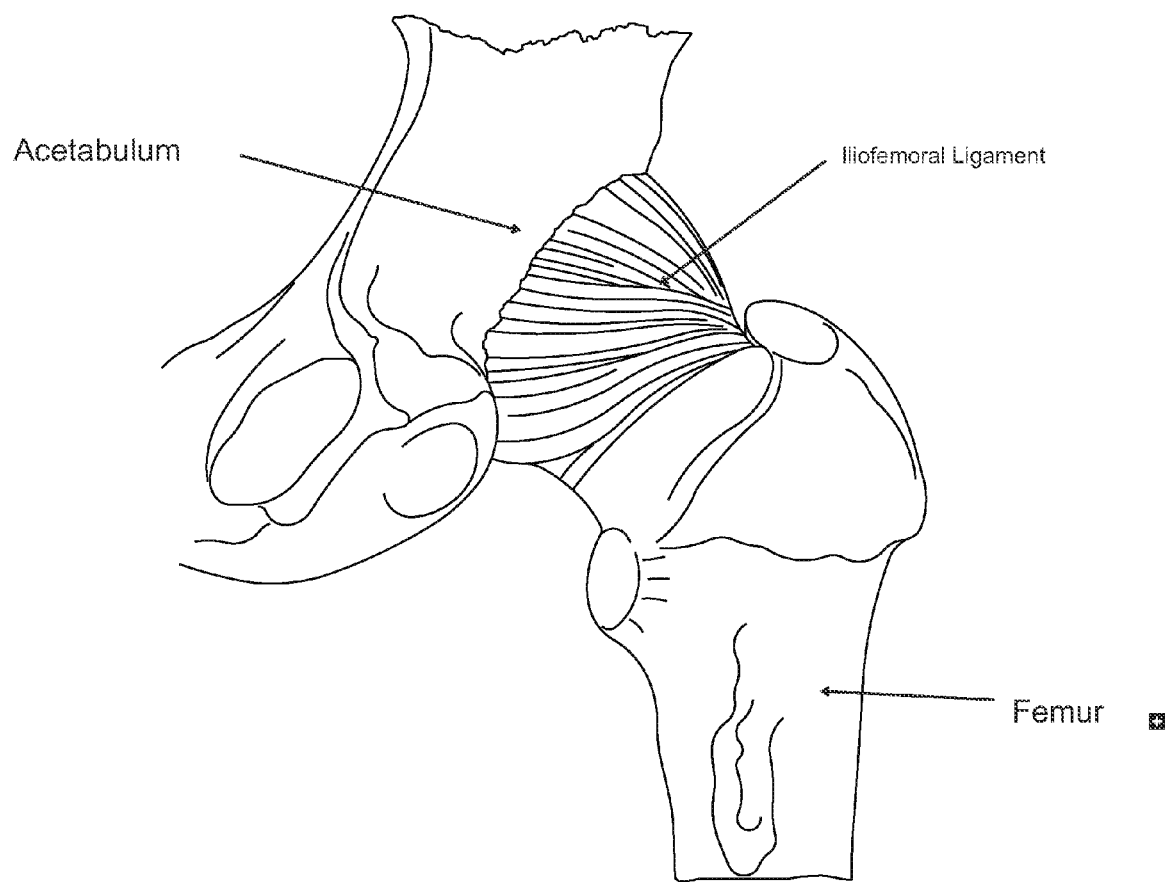
Figure 13:
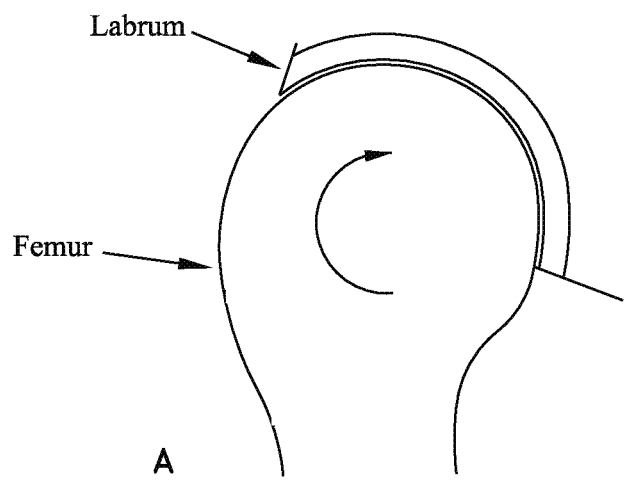
FIG. 13 is a schematic view showing cam-type femoroacetabular impingement (FAI)
Figure 13:
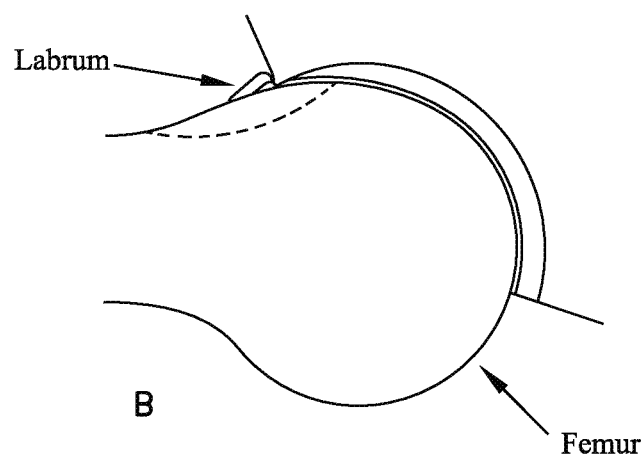
Figure 14:
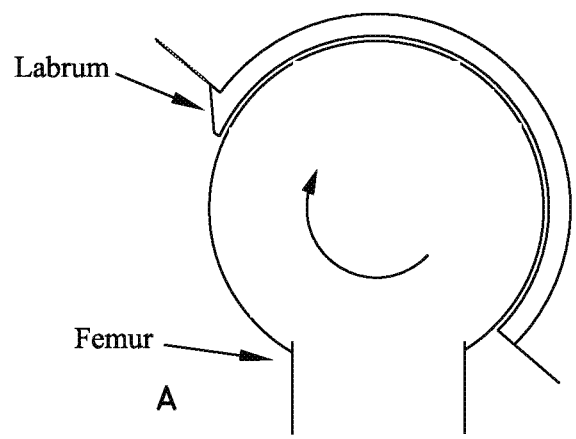
FIG. 14 is a schematic view showing pincer-type femoroacetabular impingement (FAI)
Figure 14:
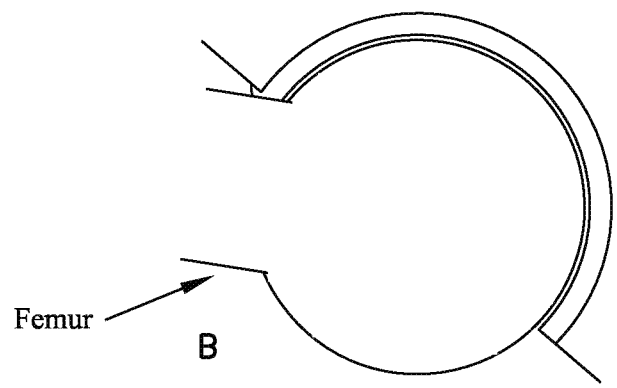
Figure 15:
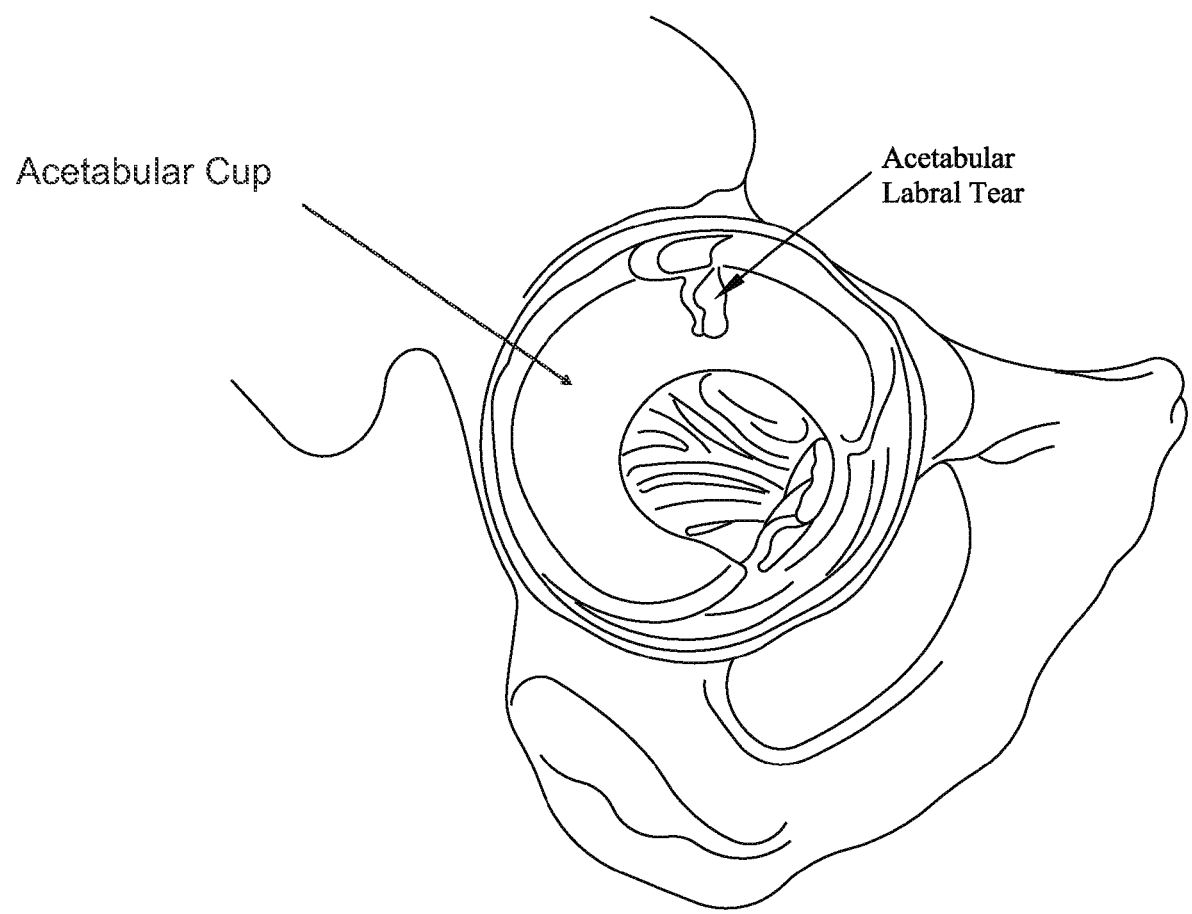
FIG. 15 is a schematic view showing a labral tear.
Figure 16:
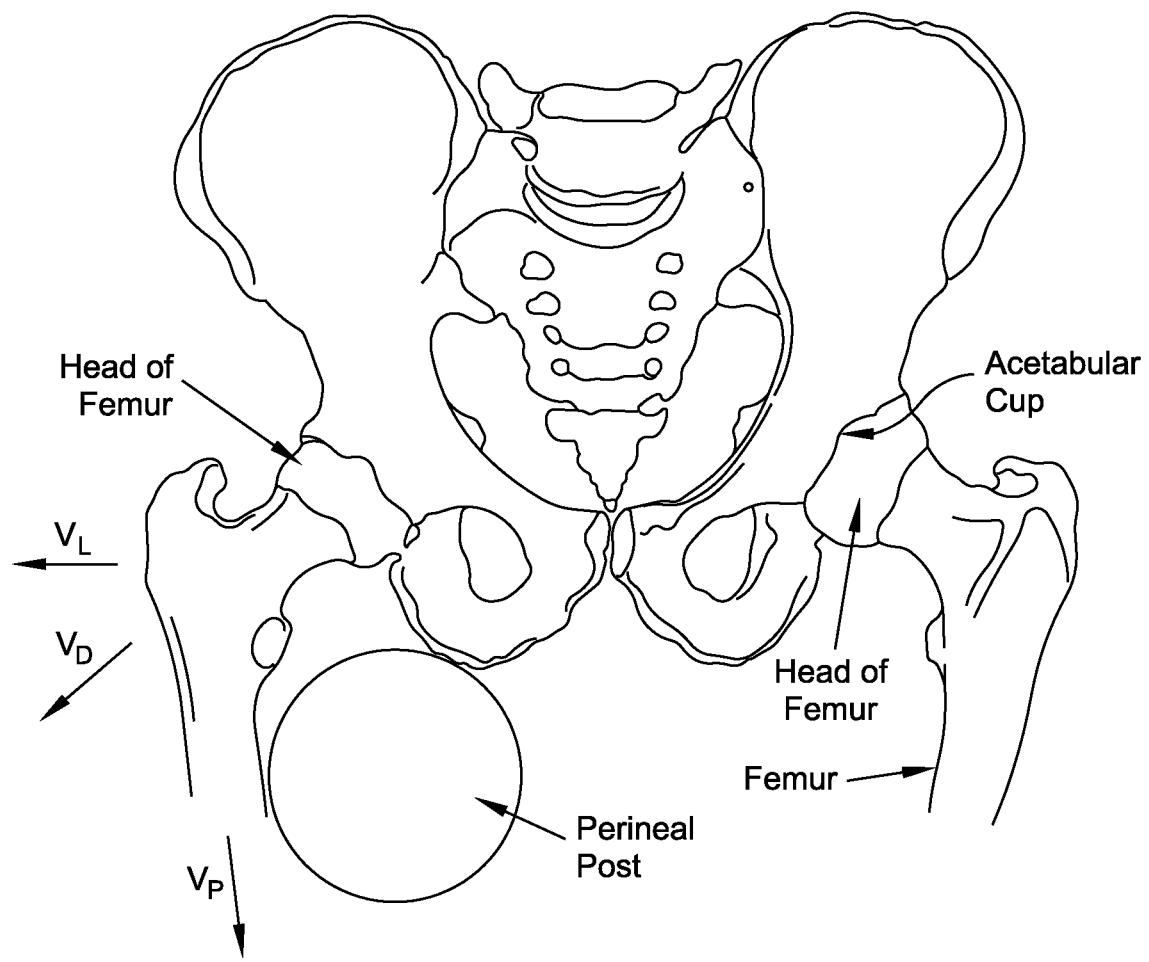
FIG. 16 is a schematic view showing how a perineal post is used to distract the hip joint in a conventional hip distraction.
Figure 20:
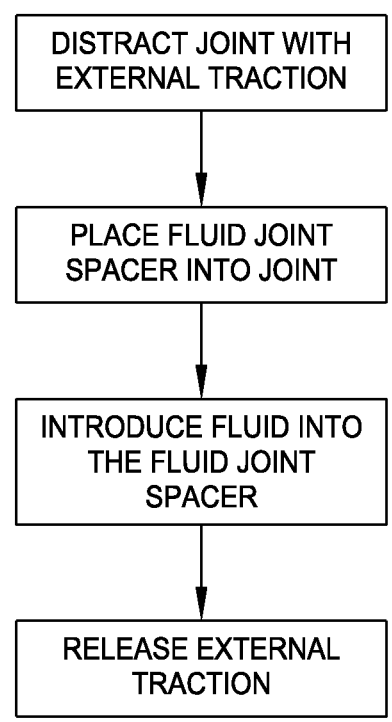

More particularly, in this form of the invention, and looking now at FIG. 20, the hip joint is first distracted using a standard leg distraction technique, e.g., by positioning a perineal post between the patient's legs, pulling on the distal end of the leg with a substantial force, and then adducting the leg so as to unseat the ball of the femur from the acetabular cup, in the manner described above and shown in FIG. 16.

Next, fluid joint spacer 5, with the balloon structure of body 15 set in its deflated state, is inserted into the space created between the ball of the femur and the acetabular cup. See FIG. 17. This may be done under direct visualization (i.e., using an endoscope inserted into the distracted joint), or under fluoroscopy, or both.

Then the balloon structure of body 15 is inflated by introducing pressurized fluid into fluid fitting 30, whereupon the pressurized fluid will flow through lumen 25 and out openings 45, whereby to apply pressure against the head of the femur and/or the acetabular cup. See FIGS. 18 and 19. This fluid is introduced into fluid fitting 30 with a sufficiently high pressure that the fluid flowing out of fluid joint spacer 5 via openings 45 is able to apply sufficient pressure to the adjacent structures so as to maintain the distraction of the joint.

Figure 21:
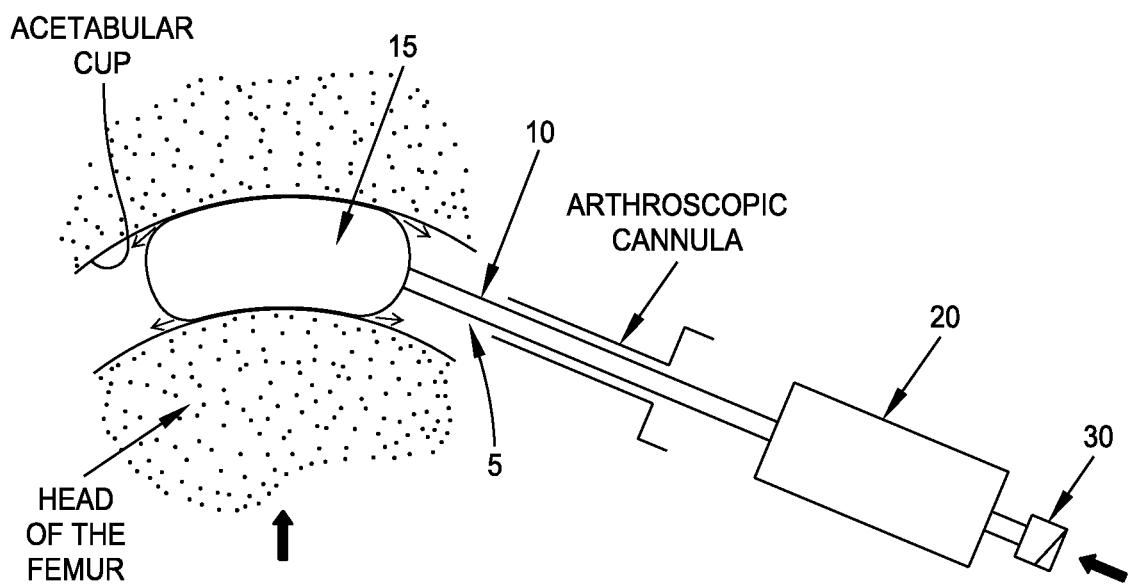

Next, the distal force which was previously applied to the distal end of the leg is partially or fully released. As this occurs, the fluid pressure applied against the head of the femur and/or the acetabular cup by fluid joint spacer 5 will maintain the distraction of the joint. See FIG. 21. Release of the full distraction force has the beneficial effect of completely eliminating the tension load imposed on the intervening tissue, whereas a partial release of the distraction force only partially eliminates the tension load imposed on the intervening tissue—however, even such partial release of the distraction force can still meaningfully reduce the tension load imposed on the intervening tissue, and it provides a safeguard in the event that the balloon structure of body 15 should prematurely deflate, e.g., mid-procedure.

Upon the aforementioned partial or full release of the external distraction force, the load of distraction is transferred to the flowing fluid bearing established between the ball of the femur and the acetabular cup, with the fluid pressure provided by fluid joint spacer 5 acting as a dynamic spacer so as to maintain a desired spacing between the ball of the femur and the acetabular cup. Thus, joint distraction is maintained even though a substantial external distraction force is no longer being applied to the distal end of the leg. Since joint distraction can be reliably maintained without the risk of damage to the intervening tissue from a substantial externally-applied distraction force, the traditional concern to complete procedures in 90 minutes or less is substantially diminished, and complications from joint distraction are greatly reduced. This is a very significant improvement over the prior art.

With the joint so distracted, the arthroscopic surgery can then proceed in the normal fashion.

Figure 22:
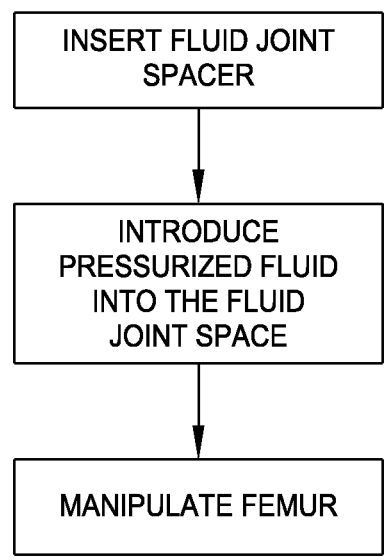

Significantly, and in accordance with another novel aspect of the invention (see FIG. 22), the use of fluid joint spacer 5 can enable the leg to be manipulated while the joint is in a distracted state. More particularly, it has been discovered that, once the balloon structure of body 15 has been inflated within the joint and the pulling force applied to the distal end of the leg has been partially or fully released, so that the aforementioned flowing fluid bearing is established between the head of the femur and the acetabular CUD, the leg can be moved about (i.e., pivoted) on the fluid joint spacer 5. Manipulation can include flexion and extension, adduction and abduction, as well as internal and external rotation. This manipulation of the leg while the joint is in a distracted, fluid-supported state enables more of the joint, anatomy and pathology to be visualized and accessed, for superior surgical results. By contrast, a patient's leg cannot be manipulated in this manner when the leg is being distracted in a conventional manner, i.e., by a pulling force applied to the distal end of the leg. Therefore, procedures can be performed using the present invention which cannot be performed using conventional distraction techniques. This is a very significant improvement over the prior art.

Figure 23:
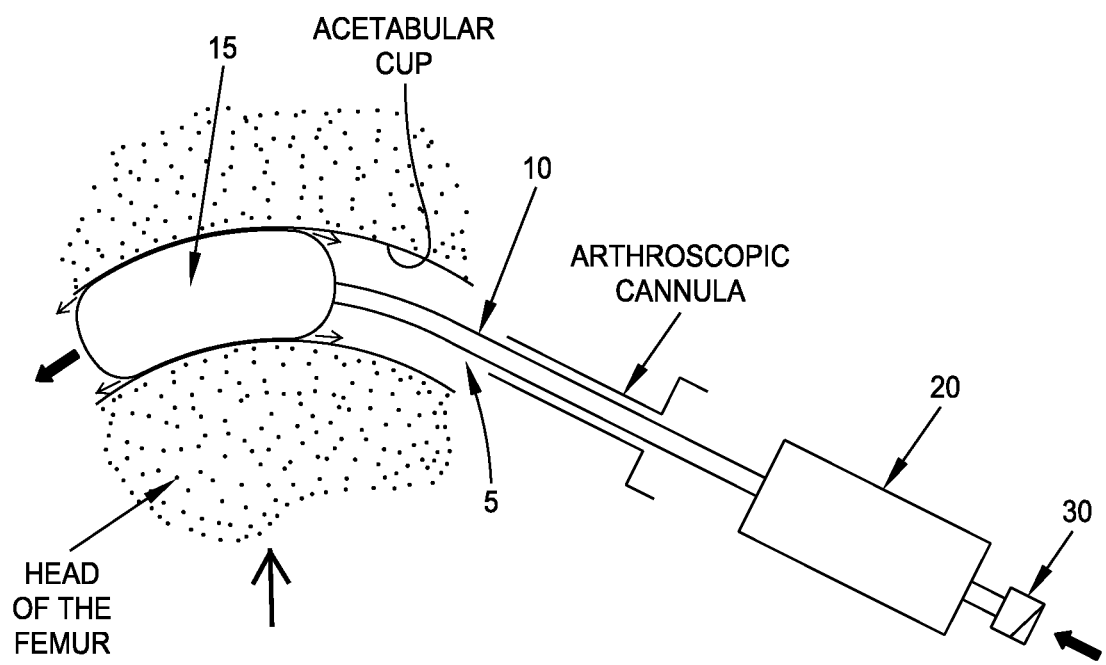
Figure 24:
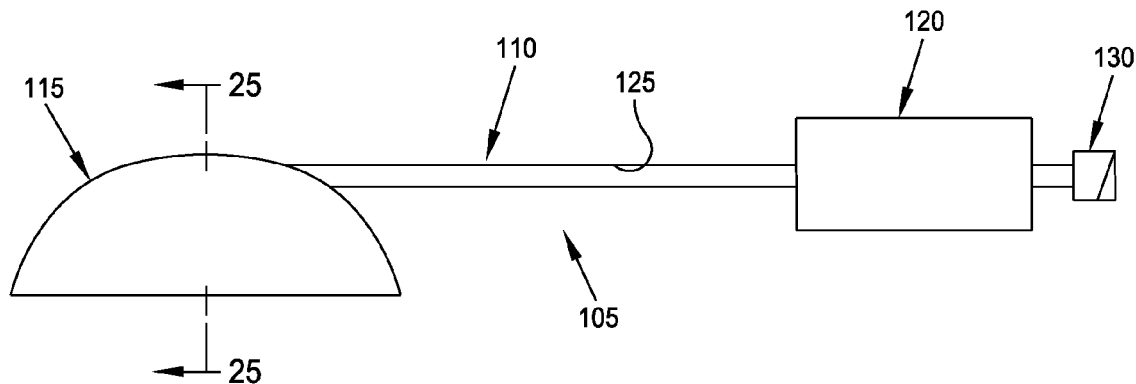
FIGS. 24-30 are schematic views showing the construction and preferred methods of use for a second embodiment of the fluid joint spacer of the present invention.
Figure 25:
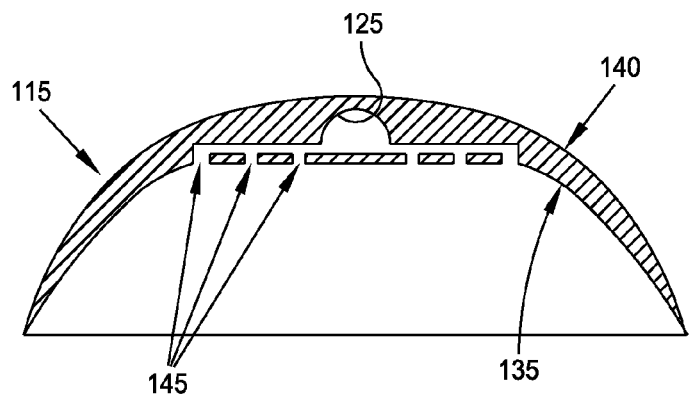
Figure 26:
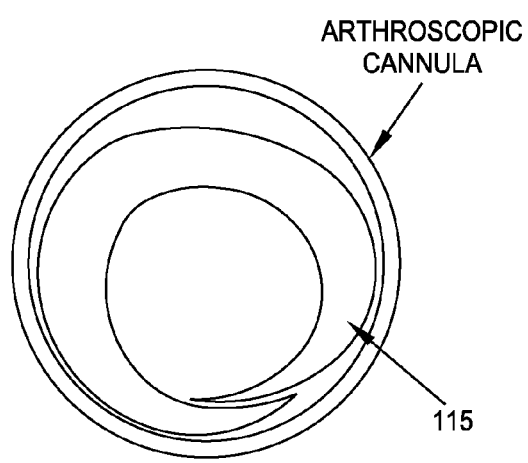
Figure 27:
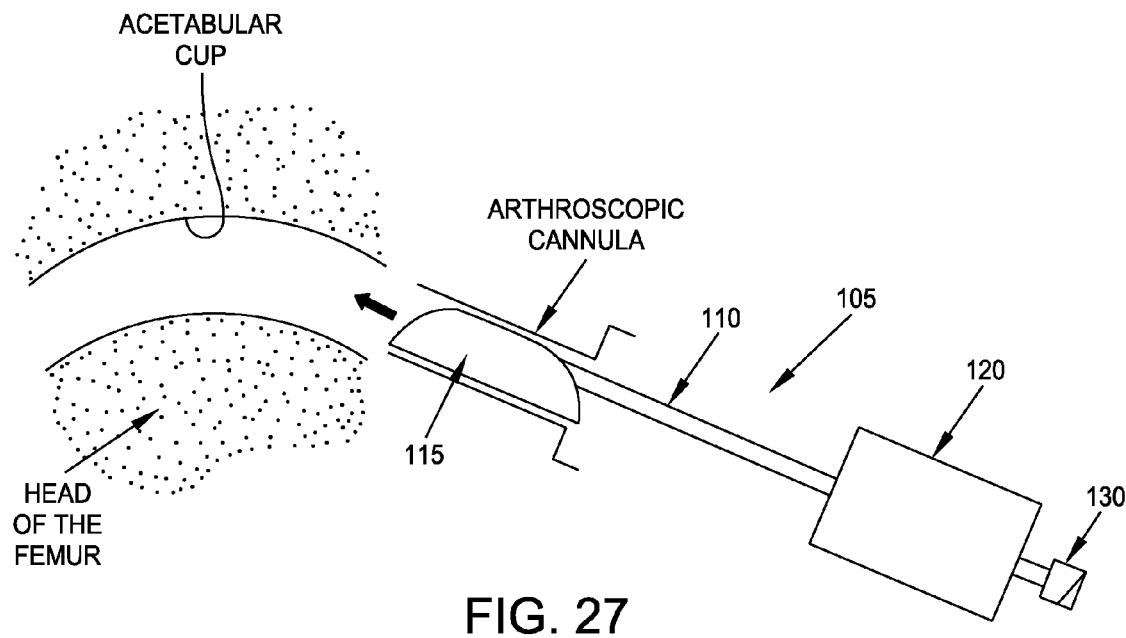
Figure 28:
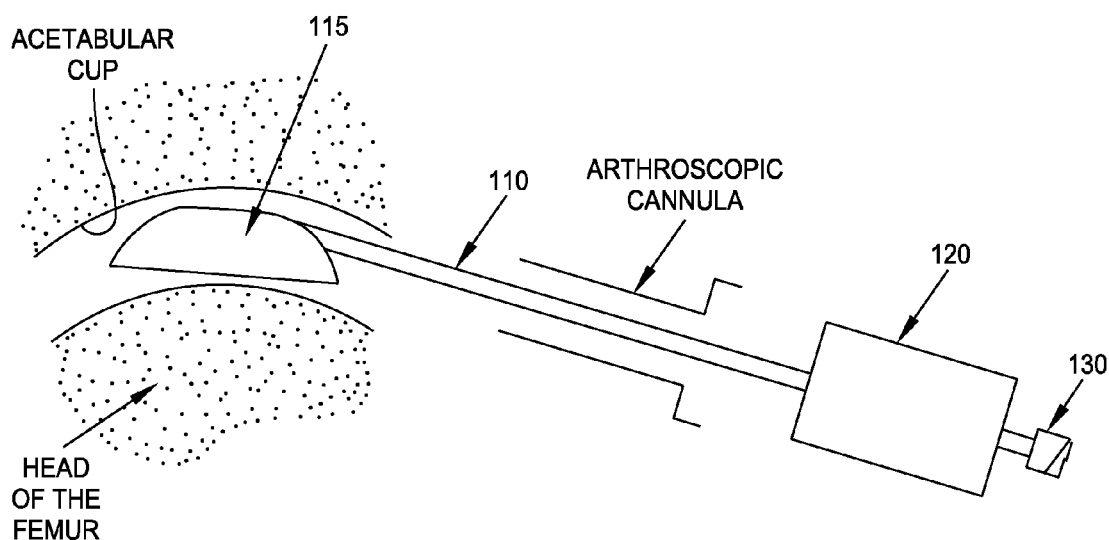
Figure 29:
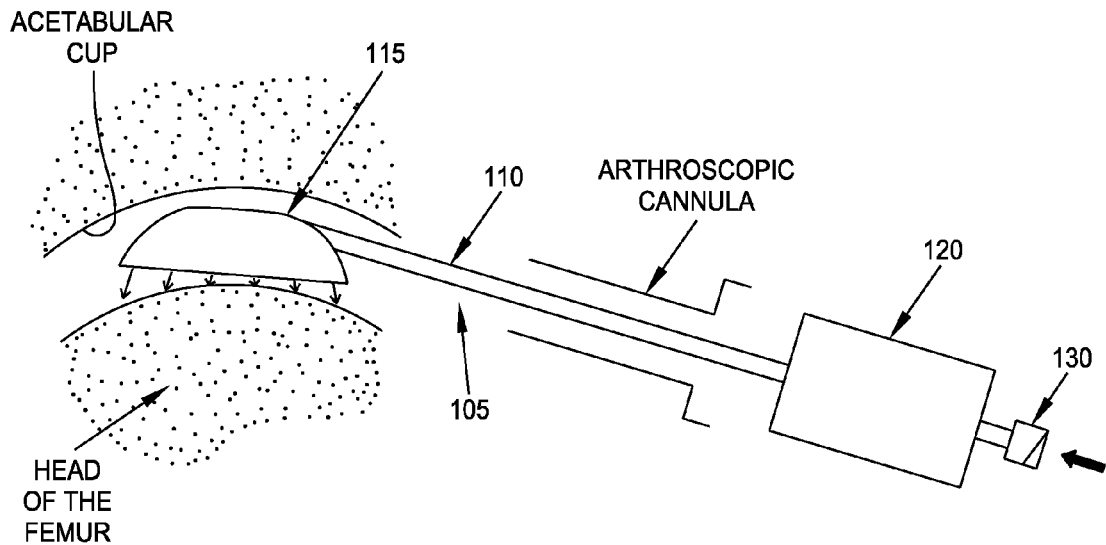
Figure 30:
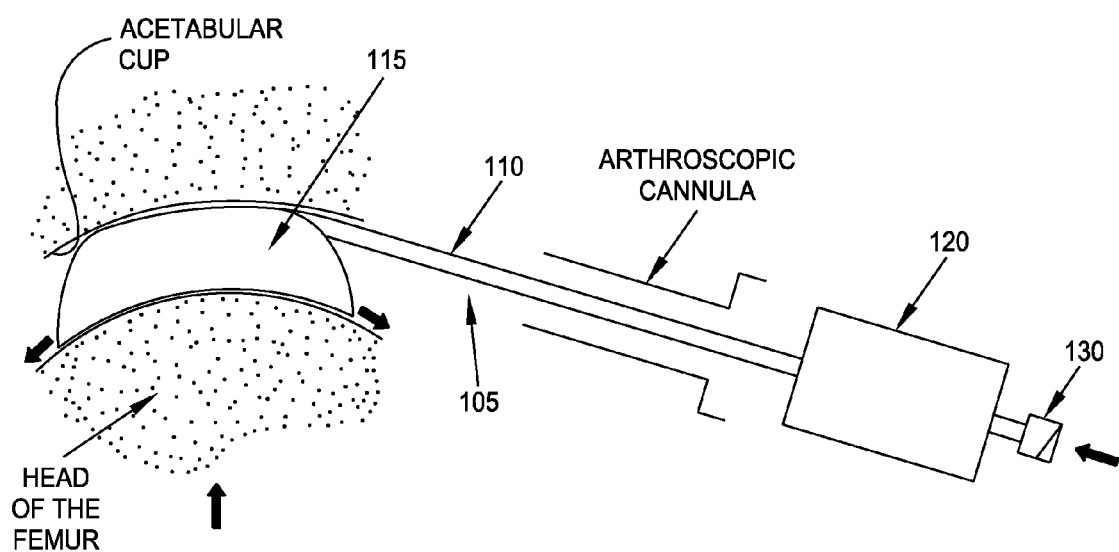
Figure 31:
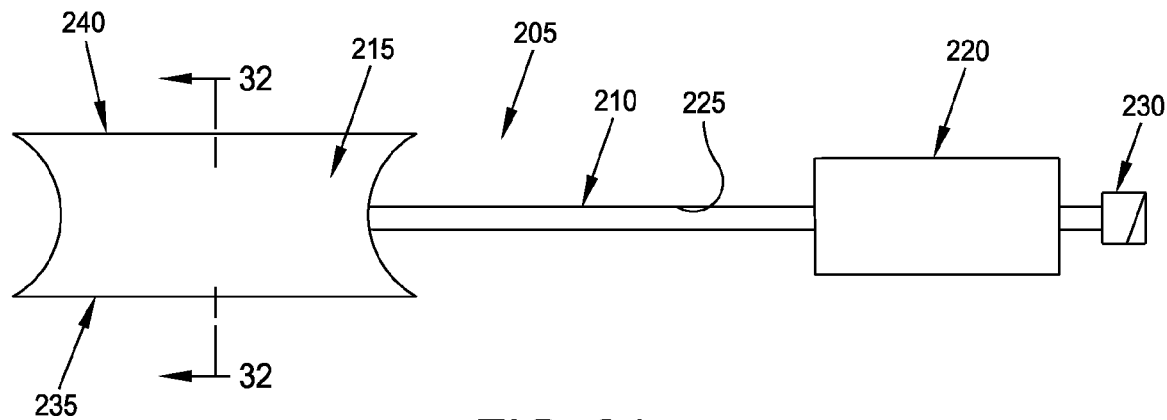
FIGS. 31-34 are schematic views showing the construction and preferred methods of use for a third embodiment of the fluid joint spacer of the present invention.
Figure 32:
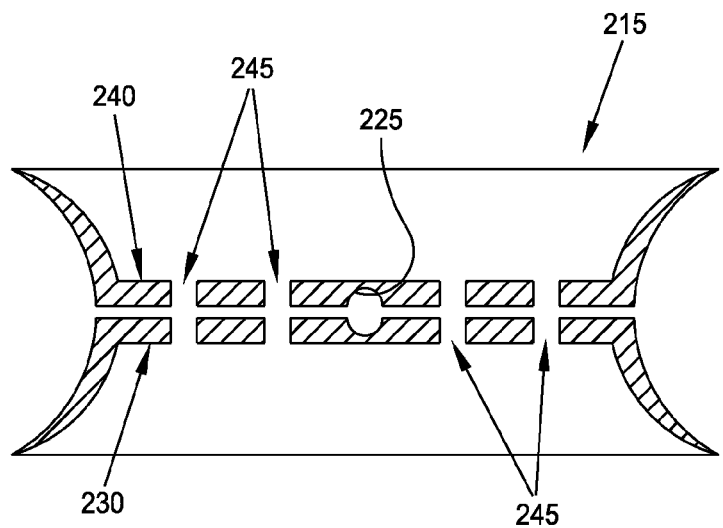
Figure 33:
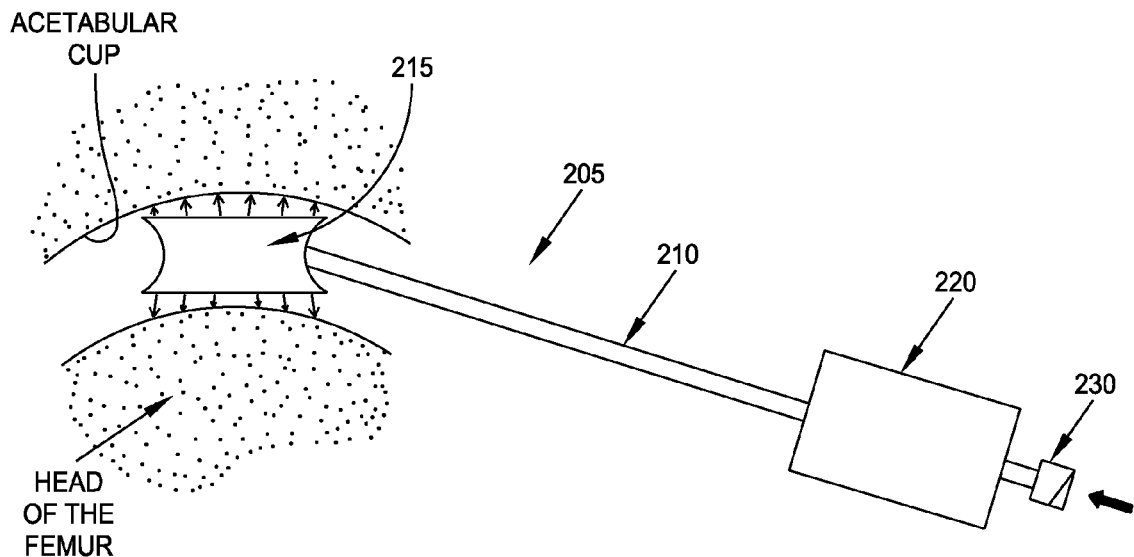
Figure 34:
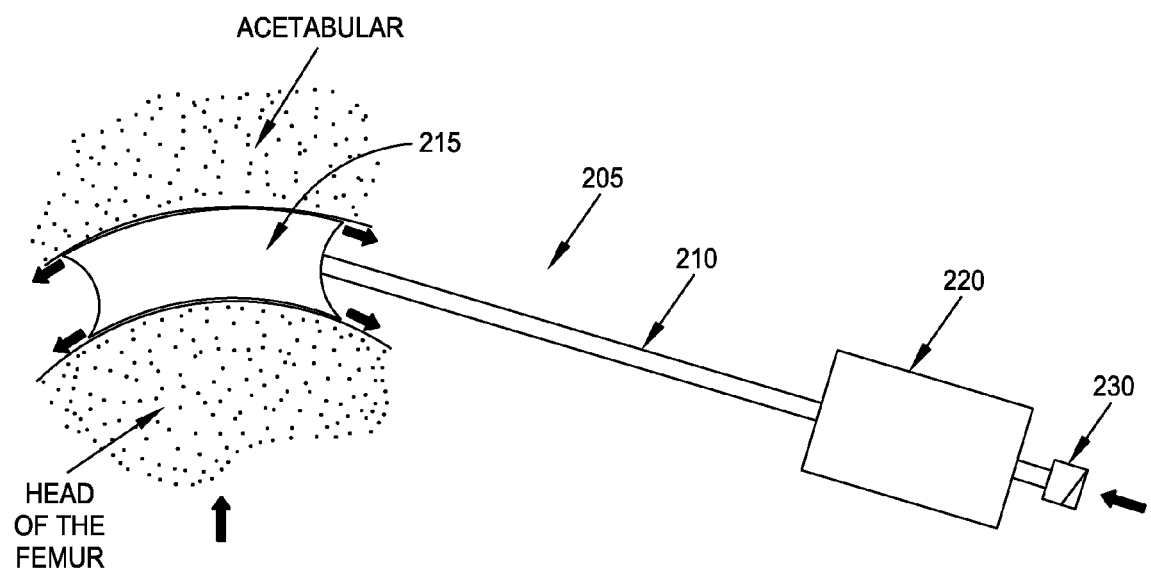

Furthermore, once distraction of the joint is being fully or partially maintained by the fluid pressure of fluid joint, spacer 5, the fluid joint spacer can itself be moved about within the joint (see FIG. 23) so as to reposition the device and/or the distracted anatomy and/or otherwise improve visualization within the joint.

Additionally, some procedures which would normally require the creation of an additional portal to access pathology can be accomplished without the creation of the additional portal, thereby reducing the visible scar and potential morbidity of the additional portal. This is also a significant improvement over the prior art.

At the conclusion of the arthoscopic surgery, a distal force is re-applied to the distal end of the leg so as to take the load off the fluid joint, spacer 5, fluid flow to fluid joint spacer 5 is stopped so that fluid pressure is no longer being applied to the head of the femur and/or the acetabular cup, and then the fluid joint spacer 5 is removed from the interior of the joint.

Finally, the distal force applied to the distal end of the leg is released, so as to allow the ball of the femur to re-seat itself in its normal position within the acetabular cup.

With respect to the foregoing method of the present invention, it should be appreciated that fluid joint spacer 5 can be specifically located in the joint space so as to preferentially bias the position of the femoral head relative to the acetabulum when the pulling force on the distal end of the leg is relaxed and the load of the joint is transferred to the fluid joint spacer. For example, positioning fluid joint spacer 5 so that body 15 is more posterior in the joint causes the femoral head to settle in a more anterior position, which can improve visualization and access to the posterior acetabular rim.

With respect to the foregoing method of the present invention, it should also be appreciated that fluid joint spacer 5 can be placed in the joint space so as to provide better visualization and access to the peripheral compartment of the hip.

Additional Constructions

It is also possible to form the fluid joint spacer with other constructions.

By way of example but not limitation, and looking now at FIGS. 24-30, there is shown a fluid joint spacer 105 which generally comprises an elongated shaft 110 having a body 115 disposed at its distal end and a handle 120 disposed at its proximal end. A lumen 125 connects the interior of body 115 with a fluid fitting 130 disposed on handle 120.

Elongated shaft 110 may be rigid or bendable and, if it is bendable, it may be steerable via means (not shown) provided on handle 120. In any case, elongated shaft 110 has sufficient structural integrity along its length so as to facilitate proper positioning of body 115 via handle 120 during use.

In this form of the invention, body 115 comprises a cup-shaped structure having a concave first surface 135 for disposition adjacent the head of the femur, and a convex second surface 140 for disposition adjacent the acetabular cup. A plurality of openings 145 are formed in concave first surface 135 and/or convex second surface 140 so that fluid introduced into fluid fitting 130 will pass through lumen 125, through body 115 and then pass out openings 145, whereby to apply fluid pressure against the head of the femur and/or the acetabular cup. In accordance with the present invention, this fluid is introduced into fluid fitting 130 with a sufficiently high pressure that the fluid flowing out of fluid joint spacer 105 via openings 145 is able to apply sufficient pressure to the adjacent structures so as to maintain the distraction of a joint into which fluid joint spacer 105 is deployed.

Body 115 may be rigid, semi-rigid or compliant, or a combination of rigid, semi-rigid or compliant. In one preferred form of the invention, body 115 is formed so that the base of the cup-shaped structure is relatively firm while the rim of the cup-shaped structure is somewhat more flexible, so that the base of the cup-shaped structure can provide support and the rim of the cup-shaped structure can conform somewhat to adjacent non-planar anatomical structures. At the same time, however, it is important that the cup-shaped structure of body 115 have enough structural integrity to accommodate the pressurized fluid of the flowing fluid bearing and direct the pressurized fluid against the appropriate anatomy, Thus, in this form of the invention, the cup-shaped structure of body 115 essentially acts as a skirt to help direct the pressurized fluid of the flowing fluid bearing against the appropriate anatomy. In one preferred form of the invention, the cup-shaped structure of body 115 is at least partially formed out of a resilient and/or elastomeric material. And in one preferred form of the invention, the cup-shaped structure of body 115 has a variable geometry comprising a thicker base and a thinner rim, so that the base has greater structural integrity and the rim is more conformable to non-planar anatomical structures.

If desired, body 115 of fluid joint spacer 105 may be foldable along its longitudinal axis (FIG. 26) so as to facilitate deployment through an arthroscopic cannula.

In one preferred method of use, the joint is distracted using conventional external traction and fluid joint, spacer 105 is advanced arthroscopically (e.g., in a folded configuration as per FIG. 26) into the distracted joint (FIGS. 27 and 28), pressurized fluid is applied to fluid fitting 130 so that pressurized fluid flows out openings 145 and against the head of the femur and/or the acetabular cup (FIG. 29), and then the external traction is partially or fully released so that the joint is thereafter supported by the flowing fluid bearing provided by fluid joint spacer 105 (FIG. 30), with fluid joint spacer 105 conforming to the non-planar surface of the joint.

In another form of the invention, the fluid joint spacer comprises a double concave configuration. More particularly, and looking now at FIGS. 31-34, there is shown a fluid joint spacer 205 which generally comprises an elongated shaft 210 having a body 215 disposed at its distal end and a handle 220 disposed at its proximal end. A lumen 225 connects the interior of body 215 with a fluid fitting 230 disposed on handle 220.

Elongated shaft 210 may be rigid or bendable and, if it is bendable, it may be steerable via means (not shown) provided on handle 220. In any case, elongated shaft 210 has sufficient structural integrity along its length so as to facilitate proper positioning of body 215 via handle 220 during use.

In this form of the invention, body 215 comprises a double concave configuration having a concave first surface 235 for disposition adjacent the head of the femur, and a concave second surface 240 for disposition adjacent the acetabular cup. A plurality of openings 245 are formed in concave first surface 235 and/or concave second surface 240 so that fluid introduced into fluid fitting 230 will pass through lumen 225, through body 215 and then pass out openings 245, whereby to apply fluid pressure against the head of the femur and/or the acetabular cup. In accordance with the present invention, this fluid is introduced into fluid fitting 230 with a sufficiently high pressure that the fluid flowing out of fluid joint spacer 205 via openings 245 is able to apply sufficient pressure to the adjacent structures so as to maintain the distraction of a joint into which fluid joint spacer 205 is deployed Body 215 may be rigid, semi-rigid or compliant, or a combination of rigid, semi-rigid or compliant. In one preferred form of the invention, body 215 is formed so that the base of the double concave structure is relatively firm while the rims of the double concave structure are somewhat more flexible, so that the base of the double concave structure can provide support and the rims of the double concave structure can conform somewhat to adjacent non-planar anatomical structures. At the same time, however, it is important that the double concave structure of body 215 have enough structural integrity to accommodate the pressurized fluid of the flowing fluid bearing and direct that pressurized fluid against the appropriate anatomical structures. Thus, in this form of the invention, the double concave structure of body 215 essentially acts as a pair of skirts to help direct the pressurized fluid of the flowing fluid bearing against the appropriate anatomy. In one preferred form of the invention, the double concave structure of body 215 is at least partially formed out of a resilient and/or elastomeric material. And in one preferred form of the invention, the double concave structure of body 215 has a variable geometry comprising a thicker base and thinner rims, so that the base has greater structural integrity and the rims are more conformable to non-planar anatomical structures.

In one preferred method of use, the joint is distracted using conventional external traction and fluid joint spacer 205 is advanced arthroscopically into the distracted joint, pressurized fluid is applied to fluid fitting 230 so that pressurized fluid flows out openings 245 and against, the head of the femur and/or the acetabular cup (FIG. 33), and then the external traction is partially or fully released so that the joint is thereafter supported by the flowing fluid bearing provided by fluid joint spacer 105 (FIG. 34) with fluid joint spacer 205 conforming to the non-planar surface of the joint.

Thus it will be seen that the present invention provides a safe and simple way to significantly reduce trauma to intervening tissue in the leg when practicing leg distraction, since a substantial distally-directed force only needs to be applied to the distal end of the patient's leg long enough for the fluid joint spacer to be positioned in the distracted joint and for the fluid joint spacer to thereafter apply fluid pressure to the head of the femur and/or the acetabular cup—the distally—directed distraction force does not need to be maintained on the distal end of the patient's leg during the surgery itself. As a result, trauma to the intervening tissue is greatly reduced, and the surgeon no longer needs to limit the duration of distraction to 90 minutes or less in order to avoid damage to the intervening tissue. This is a very significant improvement over the prior art.

In addition, the use of the present invention enables more of the joint anatomy and pathology to be visualized and accessed, since establishing the flowing fluid bearing between the ball of the femur and the acetabular CUD allows the initial external distraction to be relaxed, and allows the leg to be manipulated on the fluid joint spacer while the joint is in a distracted state. By contrast, the leg cannot be manipulated in this manner while the leg is being distracted in a conventional manner, i.e., by a pulling force applied to the distal end of the leg. Therefore, arthroscopic procedures can be performed using the present invention which cannot be performed using conventional distraction techniques. This is a very significant improvement over the prior art.

Additionally, some procedures which would normally require the creation of an additional portal to access pathology can be accomplished without the creation of the additional portal, thereby reducing the visible scar and potential morbidity of the additional portal. This is also a significant improvement over the prior art.

External Distraction of the Limb

In the foregoing description, the external distraction of the limb is generally discussed in the context of applying a distally-directed distraction force to the distal end of the leg. However, it should be appreciated that the distally-directed distraction force may be applied to another portion of the leg, e.g., to an intermediate portion of the leg, such as at or about the knee. Thus, as used herein, the term "distal end of the leg" is meant to include substantially any portion of the leg which is distal to the ball of the femur, such that by applying the external distraction force to the leg, a tension load is imposed on the intervening tissue. Furthermore, as used herein, the term "intervening tissue" is intended to mean the tissue which is interposed between the location where the external distraction force is applied to the leg and the ball of the femur.

Use of the Fluid Joint Spacer to Establish Distraction

In the foregoing description, the fluid joint spacer is discussed in the context of maintaining the distraction of a joint, where the distraction has already been established using conventional external distraction. However, it should also be appreciated that the fluid joint spacer may also be used to establish the joint distraction. In this form of the invention, the fluid joint, spacer is inserted into the undistracted joint and then pressurized fluid is applied to the fluid fitting of the device so that pressurized fluid is applied against, the head of the femur and/or the acetabular cup, whereby to distract the joint.

Use of the Present Invention for Other Applications

It should be appreciated that the present invention may be used for distracting the hip joint in an open, more invasive procedure. The present invention can also be used in hip joint pathologies where joint, distraction is not needed but space creation is needed, e.g., to visualize and/or to address pathologies in the peripheral compartment or pathologies in the peritrochanteric space. Additionally, the present invention may be used for distracting joints other than the hip joint (e.g., it may be used to distract the shoulder joint).

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method for creating space in a joint, the method comprising:

applying force to a body part so as to distract the joint and create an intra joint space;

establishing a flowing fluid bearing within the intra joint space by directing a flowing stream of fluid directly against a surface of the joint so as to apply a distracting force to the surface of the joint; and reducing the force applied to the body part so that the joint is supported by the distracting force applied by the flowing fluid bearing.

2. A method according to claim 1 wherein reducing the force applied to the body part comprises completely eliminating the force applied to the body part.

3. A method according to claim 1 wherein reducing the force applied to the body part comprises reducing, but not completely eliminating, the force applied to the body part.

4. A method according to claim 1 including the further step of performing a surgical procedure on the joint after creating an intra joint space.

5. A method according to claim 1 including the further step of moving the body part after creating an intrajoint space, so that the joint articulates on the flowing fluid bearing.

6. A method according to claim 5 wherein the geometry of the intra joint space is modified when the joint articulates on the flowing fluid bearing.

7. A method according to claim 5 including the additional step of performing a surgical procedure on the joint after the joint articulates on the flowing fluid bearing.

8. A method according to claim 1 including the further step of moving the flowing fluid bearing after creating an intrajoint space.

9. A method according to claim 8 wherein the geometry of the intra joint space is modified when the flowing fluid bearing is moved.

10. A method according to claim 8 including the additional step of performing a surgical procedure on the joint after the flowing fluid bearing is moved.

11. A method according to claim 1 wherein the joint is the hip joint.

12. A method according to claim 1 wherein the body part is a limb.

13. A method according to claim 1 wherein the body part is a limb, and further wherein the force is applied to the distal end of the limb.

14. A method according to claim 1 wherein the body part is a limb, and further wherein the force is applied to an intermediate portion of the limb.

15. A method according to claim 1 wherein the flowing fluid bearing comprises a body emitting pressurized fluid flow.

16. A method according to claim 15 wherein the body comprises a first surface and a second surface, and further wherein the body emits pressurized fluid flow from at least one of the first surface and the second surface.

17. A method according to claim 16 wherein the body emits pressurized fluid from both the first surface and the second surface.

18. A method according to claim 16 wherein at least one of the first surface and the second surface is substantially planar.

19. A method according to claim 16 wherein at least one of the first surface and the second surface is concave.

20. A method according to claim 16 wherein at least one of the first surface and the second surface is convex.

21. A method according to claim 16 wherein the first surface is concave and the second surface is convex.

22. A method according to claim 15 wherein the body comprises an inflatable member.

23. A method according to claim 15 wherein the fluid is saline.

24. A method according to claim 15 wherein the fluid is air.

25. A method according to claim 15 wherein the body is disposed at the distal end of a shaft.

26. A method according to claim 25 wherein at least a portion of the shaft is flexible.

27. A method according to claim 25 wherein the shaft is steerable.

28. A method according to claim 25 wherein the shaft is adapted to ride on a guidewire.

29. A method according to claim 25 wherein pressurized fluid flow is applied to the proximal end of the shaft, flows through the shaft and is emitted from the body.

30. A method according to claim 25 wherein the proximal end of the shaft comprises a handle.

31. A method according to claim 15 wherein the body comprises a material selected from the group consisting of a rigid material, a semi-rigid material and a compliant material.

32. A method according to claim 15 wherein the body comprises at least one concave structure including a base and a rim, and further wherein the rim is more compliant than the base.

33. A method according to claim 32 wherein the at least one concave structure acts as a skirt to help direct pressurized fluid against adjacent anatomy.

34. A method according to claim 32 wherein the body comprises two concave structures.

35. A method according to claim 15 wherein the body is capable of folding along an axis.

36. A method according to claim 1 wherein the body is delivered to the intra joint space by passing the body through an arthroscopic cannula.

37. A method according to claim 1 wherein the body part is a limb, and further wherein applying a force to a body part so as to distract the joint and create an intra joint space comprises:

(i) positioning a post adjacent to the body part; and
(ii) applying a force to the limb at a location remote from the post, the force having a distally-directed vector and a laterally-directed vector, so that the post acts as a fulcrum to distract the joint and create an intra joint space.

38. A method for creating space in a joint, the method comprising:

inserting a fluid joint spacer into the interior of the joint; and passing pressurized fluid through the fluid joint spacer and directing a flowing stream of fluid against a surface of the joint so as to apply a distracting force to the surface of the joint, whereby so as to create an intra joint space.

39. A method according to claim 38 including the further step of performing a surgical procedure on the joint after creating an intra joint space.

40. A method according to claim 38 including the further step of moving the body part after creating an intra joint space, so that the joint articulates on the flowing fluid bearing.

41. A method according to claim 40 wherein the geometry of the intra joint space is modified when the joint articulates on the flowing fluid bearing.

42. A method according to claim 40 including the additional step of performing a surgical procedure on the joint after the joint articulates on the flowing fluid bearing.

43. A method according to claim 38 including the further step of moving the flowing fluid bearing after creating an intra joint space.

44. A method according to claim 43 wherein the geometry of the intra joint space is modified when the flowing fluid bearing is moved.

45. A method according to claim 43 including the additional step of performing a surgical procedure on the joint after the flowing fluid bearing is moved.

46. A method according to claim 38 wherein the flowing fluid bearing comprises a body emitting pressurized fluid flow.

47. A method according to claim 46 wherein the body comprises a first surface and a second surface, and further wherein the body emits pressurized fluid flow from at least one of the first surface and the second surface.

48. A method according to claim 47 wherein the body emits pressurized fluid from both the first surface and the second surface.

49. A method according to claim 47 wherein at least one of the first surface and the second surface is substantially planar.

50. A method according to claim 46 wherein the body comprises an inflatable member.

51. A method according to claim 46 wherein the fluid is saline.

52. A method according to claim 46 wherein the body is disposed at the distal end of a shaft.

53. A method according to claim 52 wherein at least a portion of the shaft is flexible.

54. A method according to claim 52 wherein the shaft is steerable.

* * * * *